(12) United States Patent
Hosokawa et al.

(10) Patent No.: US 8,058,450 B2
(45) Date of Patent: Nov. 15, 2011

(54) NITROGENOUS HETEROCYCLIC DERIVATIVE AND ORGANIC ELECTROLUMINESCENCE DEVICE MAKING USE OF THE SAME

(75) Inventors: Chishio Hosokawa, Chiba (JP); Hiroshi Yamamoto, Chiba (JP); Takashi Arakane, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 780 days.

(21) Appl. No.: 11/997,916

(22) PCT Filed: Jul. 7, 2006

(86) PCT No.: PCT/JP2006/313596
§ 371 (c)(1),
(2), (4) Date: Mar. 27, 2008

(87) PCT Pub. No.: WO2007/018007
PCT Pub. Date: Feb. 15, 2007

(65) Prior Publication Data
US 2008/0284322 A1    Nov. 20, 2008

(30) Foreign Application Priority Data
Aug. 5, 2005 (JP) .................................. 2005-227615

(51) Int. Cl.
*C07D 403/10* (2006.01)
*C07D 235/18* (2006.01)
*C07D 235/08* (2006.01)

(52) U.S. Cl. .................................. 548/305.4; 548/310.7

(58) Field of Classification Search ........................ None
See application file for complete search history.

(56) References Cited

U.S. PATENT DOCUMENTS

| 5,645,948 A | 7/1997 | Shi et al. | |
| 2006/0147747 A1* | 7/2006 | Yamamoto et al. | 428/690 |
| 2007/0200490 A1* | 8/2007 | Kawamura et al. | 313/504 |
| 2007/0267970 A1* | 11/2007 | Yamamoto et al. | 313/506 |
| 2010/0193773 A1* | 8/2010 | Yamamoto et al. | 257/40 |

FOREIGN PATENT DOCUMENTS

| JP | 2002 038141 | 2/2002 |
| JP | 2004 352655 | 12/2004 |
| WO | 2004 080975 | 9/2004 |
| WO | 2005 042176 | 5/2005 |
| WO | 2005 042614 | 5/2005 |

* cited by examiner

*Primary Examiner* — Kamal Saeed
*Assistant Examiner* — Nyeemah A Grazier
(74) *Attorney, Agent, or Firm* — Oblon, Spivak, McClelland, Maier & Neustadt, L.L.P.

(57) ABSTRACT

A novel nitrogen-containing heterocyclic compound having a specific structure and an organic electroluminescence device comprising an anode, a cathode and an organic thin film layer which comprises a single layer or a plurality of layers comprising at least a light emitting layer and is disposed between the anode and the cathode, wherein at least one layer in the organic thin film layer comprises the above nitrogen-containing heterocyclic derivative singly or as a component of a mixture. The organic electroluminescence device exhibits a great luminance of emitted light and a great efficiency of light emission even under application of a low voltage.

7 Claims, No Drawings

NITROGENOUS HETEROCYCLIC DERIVATIVE AND ORGANIC ELECTROLUMINESCENCE DEVICE MAKING USE OF THE SAME

TECHNICAL FIELD

The present invention relates to a novel nitrogenous ("nitrogenous" will be occasionally referred to as "nitrogen-containing", hereinafter) heterocyclic derivative and an electroluminescence ("electroluminescence" will be occasionally referred to as "EL" hereinafter) device using the derivative; and more particularly to an organic EL device which exhibits a great luminance of emitted light and a great efficiency of light emission even under application of a low voltage since a nitrogen-containing heterocyclic derivative useful as a component constituting an organic EL device is used as a material for the EL device comprised in an organic thin film layer.

BACKGROUND ART

Organic EL devices using organic substances are expected to be useful as the inexpensive full color display device of the solid light emission type having a great area, and various developments have been made. In general, an EL device is constituted with a light emitting layer and a pair of electrodes disposed at both sides of the light emitting layer. For the light emission, electrons are injected at the side of the cathode, and holes are injected at the side of the anode when an electric field is applied. The electrons are combined with the holes in the light emitting layer to form excited states, and the energy formed when the excited states returns to the ground state is discharged as light.

Conventional organic EL devices require greater driving voltages and exhibit smaller luminances of emitted light and smaller efficiencies of light emission than those of inorganic light emitting diodes. Moreover, marked deterioration in the properties takes place, and the devices have not been used in practical applications. The properties of the organic EL devices are being improved gradually, but a greater luminance of emitted light and a greater efficiency of light emission under application of a low voltage are required.

To overcome the above problem, for example, a device using a compound having the benzimidazole structure as the light emitting material is disclosed in Patent Reference 1, and it is described that the device emits light at a luminance of 200 nit under a voltage of 9 V. In Patent Reference 2, a compound having the benzimidazole ring and the anthracene skeleton structure is described. However, an organic EL device exhibiting a greater luminance of emitted light and a greater efficiency of light emission than those obtained by the organic EL devices using the above compounds is required.

[Patent Reference 1] U.S. Pat. No. 5,645,948
[Patent Reference 1] Japanese Patent Application Laid-Open No. 2002-38141

DISCLOSURE OF THE INVENTION

Problems to be Overcome by the Invention

The present invention has been made to overcome the above problems and has an object of providing an organic EL device which exhibits a great luminance of emitted light and a great efficiency of light emission even under application of a low voltage and a nitrogen-containing heterocyclic derivative which enables to obtain the organic EL device.

Means for Overcoming the Problems

As the result of intensive studies by the present inventors to achieve the above object, it was found that a great luminance of emitted light and a great efficiency of light emission could be achieved even under application of a low voltage by using a novel compound, which is a nitrogen-containing heterocyclic derivative having a structure in which benzimidazole and a specific group are bonded together, in at least one layer in organic compound layers of an organic EL device as a material for the organic EL device.

The present invention provides a nitrogen-containing heterocyclic derivative represented by following general formula (1) or (2):

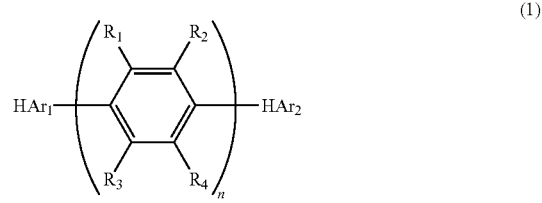

(1)

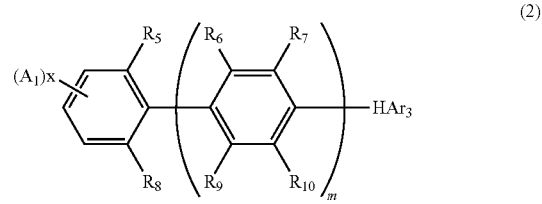

(2)

wherein $R_1$ to $R_{10}$ and $A_1$ each independently represent hydrogen atom, a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted with a substituted or unsubstituted aryl group having 5 to 50 ring atoms, a halogen atom, cyano group, nitro group, hydroxy group or carboxy group;

in general formula (1), at least one pair of substituents selected from a pair of $R_1$ and $R_2$ being bonded to an adjacent benzene ring, and a pair of $R_3$ and $R_4$ being bonded to an adjacent benzene ring, are bonded to each other to form a substituted or unsubstituted ring; in general formula (2), at least one pair of substituents selected from a pair of $R_6$ and $R_7$ being bonded to an adjacent benzene ring, and a pair of $R_9$ and $R_{10}$ being bonded to an adjacent benzene ring, are bonded to each other to form a substituted or unsubstituted ring; and pairs of substituents represented by $R_1$ and $R_2$, $R_3$ and $R_4$, $R_6$ and $R_7$, and $R_9$ and $R_{10}$, which are each bonded to a same benzene ring, may be bonded to each other to form a substituted or unsubstituted ring;

n represents an integer of 3 to 6, m represents an integer of 2 to 5, and x represents an integer of 0 to 3;

when any of substituents represented by $R_1$ to $R_{10}$ and $A_1$ is present in plurality, the plurality of substituents may be same with or different from each other; and HAr₁ to HAr₃ each independently represents a monovalent group formed by removing any one of substituents represented by $R_{1a}$ to $R_{6a}$ from a nitrogen-containing heterocyclic structure represented by general formula (a):

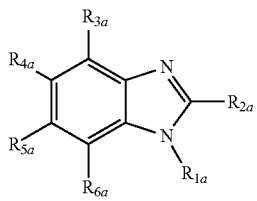

(a)

in general formula (a), $R_{1a}$ to $R_{6a}$ each independently representing hydrogen atom, a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted with a substituted or unsubstituted aryl group having 5 to 50 ring atoms, a halogen atom, cyano group, nitro group, hydroxy group or carboxy group.

The present invention also provides an organic EL device comprising an anode, a cathode and an organic thin film layer which comprises a single layer or a plurality of layers comprising at least a light emitting layer and is disposed between the anode and the cathode, wherein at least one layer in the organic thin film layer comprises the nitrogen-containing heterocyclic derivative described above singly or as a component of a mixture.

EFFECT OF THE INVENTION

The organic EL device using the nitrogen-containing heterocyclic derivative of the present invention exhibits a great luminance of emitted light and a great efficiency of light emission even under application of a low voltage.

THE MOST PREFERRED EMBODIMENT TO CARRY OUT THE INVENTION

The nitrogen-containing heterocyclic derivative of the present invention is a compound represented by following general formula (1) or (2):

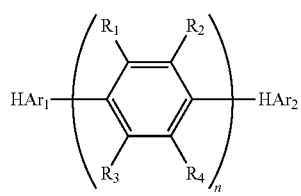

(1)

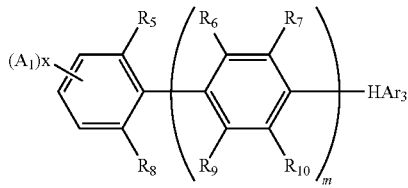

(2)

In general formulae (1) and (2), $R_1$ to $R_{10}$ and $A_1$ each independently represent hydrogen atom, a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted with a substituted or unsubstituted aryl group having 5 to 50 ring atoms, a halogen atom, cyano group, nitro group, hydroxy group or carboxy group;

The aryl group represented by $R_1$ to $R_{10}$ and $A_1$ may be any of aromatic hydrocarbon groups and aromatic heterocyclic groups, examples of which include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, fluoranthenyl group, fluorenyl group, 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Among these groups, phenyl group, naphthyl group, biphenyl group, anthryl group, phenanthryl group, pyrenyl group, chrysenyl group, fluoranthenyl group and fluorenyl group are preferable.

Examples of the alkyl group represented by $R_1$ to $R_{10}$ and $A_1$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyano-isobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The alkoxy group represented by $R_1$ to $R_{10}$ and $A_1$ is a group represented by —OY. Examples of the group represented by Y include the groups described above as the examples of the alkyl group.

Examples of the aralkyl group represented by $R_1$ to $R_{10}$ and $A_1$ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The aryloxy group represented by $R_1$ to $R_{10}$ and $A_1$ is a group represented by —OY. Examples of the group represented by Y include the groups described above as the examples of the aryl group.

The arylthio group represented by $R_1$ to $R_{10}$ and $A_1$ is a group represented by —SY'. Examples of the group represented by Y' include the groups described above as the examples of the aryl group.

The alkoxycarbonyl group represented by $R_1$ to $R_{10}$ and $A_1$ is a group represented by —COOY. Examples of the group represented by Y include the groups described above as the examples of the alkyl group.

Examples of the aryl group in the amino group substituted with an aryl group which is represented by $R_1$ to $R_{10}$ and $A_1$ include the groups described above as the examples of the aryl group.

Examples of the halogen atom represented by $R_1$ to $R_{10}$ and $A_1$ include fluorine atom, chlorine atom, bromine atom and iodine atom.

In general formula (1), at least one pair of substituents selected from a pair of $R_1$ and $R_2$ being bonded to an adjacent benzene ring, and a pair of $R_3$ and $R_4$ being bonded to an adjacent benzene ring, are bonded to each other to form a substituted or unsubstituted ring. In general formula (2), at least one pair of substituents selected from a pair of $R_6$ and $R_7$ being bonded to an adjacent benzene ring, and a pair of $R_9$ and $R_{10}$ being bonded to an adjacent benzene ring, are bonded to each other to form a substituted or unsubstituted ring. Pairs of substituents represented by $R_1$ and $R_2$, $R_3$ and $R_4$, $R_6$ and $R_7$, and $R_9$ and $R_{10}$, which are each bonded to the same benzene ring and adjacent to each other, may be bonded to each other to form a substituted or unsubstituted ring. It is preferable that the formed aromatic ring is a five-membered ring or a six-membered ring and more preferably a five-membered ring.

Substituents on the formed five-membered ring or six-membered ring may be bonded to the each other to form a ring.

Examples of the ring formed above include cyclic structures of cycloalkanes having 4 to 12 carbon atoms such as cyclobutane, cyclopentane, cyclohexane, adamantane and norbornane, cycloalkenes having 4 to 12 carbon atoms such as cyclobutene, cyclopentene, cyclohexene, cycloheptane and cyclooctene; cycloalkadienes having 6 to 12 carbon atoms such as cyclohexadiene, cycloheptadiene and cyclooctadiene, and aromatic rings having 6 to 50 carbon atoms such as benzene, naphthalene, phenanthrene, anthracene, pyrene, chrysene, acenaphthylene and fluorene.

In general formulae (1) and (2), n represents an integer of 3 to 6, preferably 3 to 5, m represents an integer of 2 to 5, preferably 2 to 4, and x represents an integer of 0 to 3, preferably 0 to 2. When any of substituents represented by $R_1$ to $R_{10}$ and $A_1$ is present in plurality, the plurality of substituents may be the same with or different from each other.

In general formulae (1) and (2), $HAr_1$ to $HAr_3$ each independently represents a monovalent group formed by removing any one of substituents represented by $R_{1a}$ to $R_{6a}$ from a nitrogen-containing heterocyclic structure represented by general formula (a):

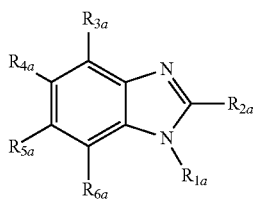

(a)

In general formula (a), $R_{1a}$ to $R_{6a}$ each independently represent hydrogen atom, a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted with a substituted or unsubstituted aryl group having 5 to 50 ring atoms, a halogen atom, cyano group, nitro group, hydroxy group or carboxy group. Examples of the above groups include the groups described as the examples of the groups represented by $R_1$ to $R_{10}$ and $A_1$.

Examples of the substituents to the groups in general formulae (1), (2) and (a) include substituted and unsubstituted aryl groups having 5 to 50 ring atoms, substituted and unsubstituted alkyl groups having 1 to 50 carbon atoms, substituted and unsubstituted alkoxy groups having 1 to 50 carbon atoms, substituted and unsubstituted aralkyl groups having 6 to 50 carbon atoms, substituted and unsubstituted aryloxy groups having 5 to 50 ring atoms, substituted and unsubstituted arylthio groups having 5 to 50 ring atoms, substituted and unsubstituted alkoxycarbonyl groups having 1 to 50 carbon atoms, amino groups substituted with a substituted or unsubstituted aryl group having 5 to 50 ring atoms, halogen atoms, cyano group, nitro group, hydroxy group and carboxy group.

It is preferable that the nitrogen-containing heterocyclic derivative represented by general formula (1) is a compound represented by following general formula (1-a), (1-b) or (1-c):

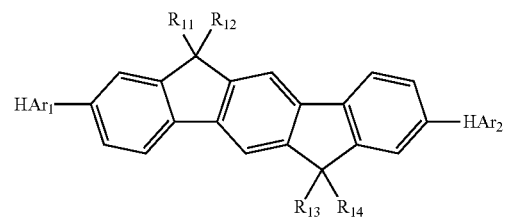

(1-a)

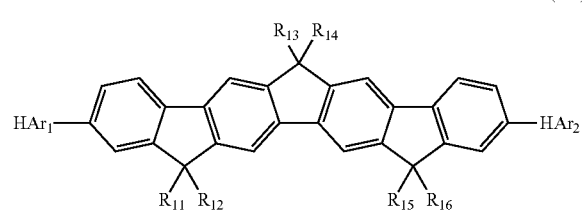

(1-b)

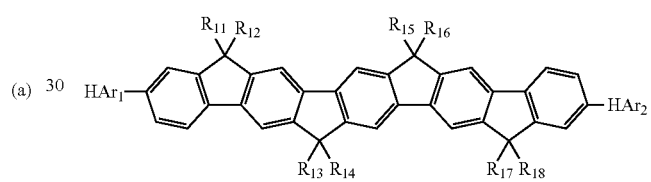

(1-c)

In general formulae (1-a), (1-b) and (1-c), $HAr_1$ and $HAr_2$ are as defined above, and $R_{11}$ to $R_{18}$ are as defined above for $R_{1a}$ to $R_{6a}$. Examples of the groups and the substituent to the groups include the groups and the substituents described above as the examples of the corresponding groups and substituents.

It is preferable that the nitrogen-containing heterocyclic derivative represented by general formula (2) is a compound represented by following general formula (2-a), (2-b) or (2-c):

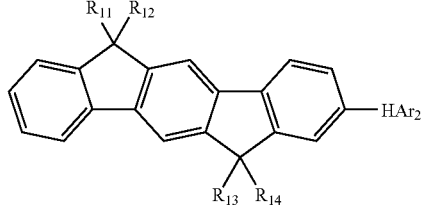

(2-a)

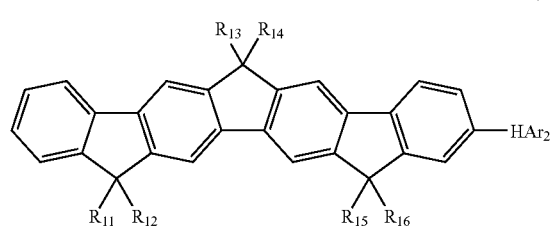

(2-b)

-continued (2-c)

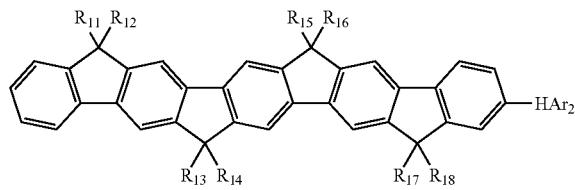

In general formulae (2-a), (2-b) and (2-c), HAr$_2$ is as defined above, and R$_{11}$ to R$_{18}$ are as defined above for R$_{1a}$ to R$_{6a}$. Examples of the groups and the substituent to the groups include the groups and the substituents described above as the examples of the corresponding groups and substituents.

It is preferable that the nitrogen-containing heterocyclic derivative of the present invention is a material for organic EL devices and, more preferably, a light emitting material for organic EL devices, an electron injecting material for organic EL devices or an electron transporting material for organic EL devices.

Examples of the nitrogen-containing heterocyclic derivative represented by general formula (1) or (2) are shown in the following. However, the nitrogen-containing heterocyclic derivative represented by general formula (1) is not limited to the compounds shown as the examples.

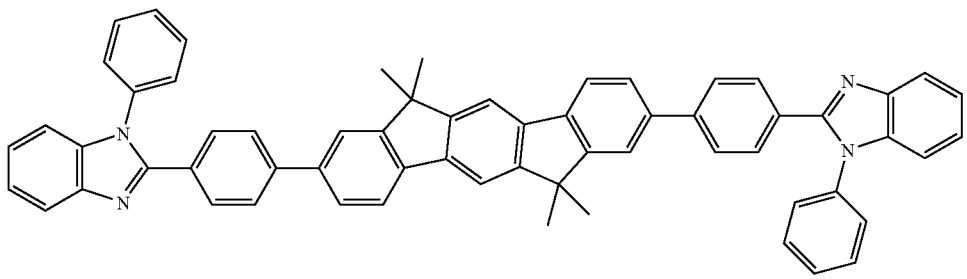

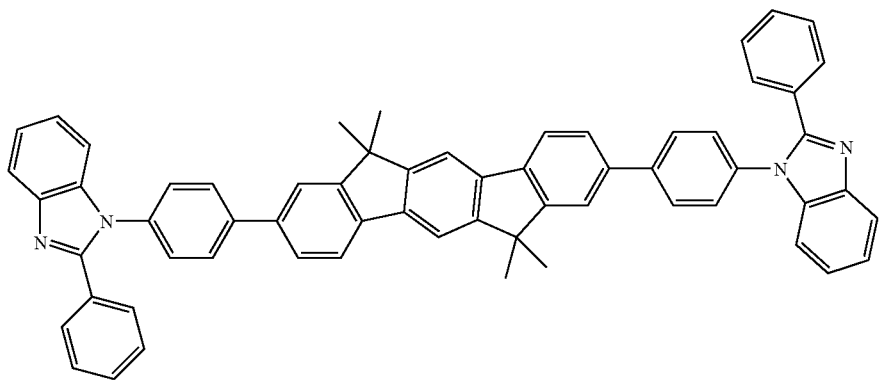

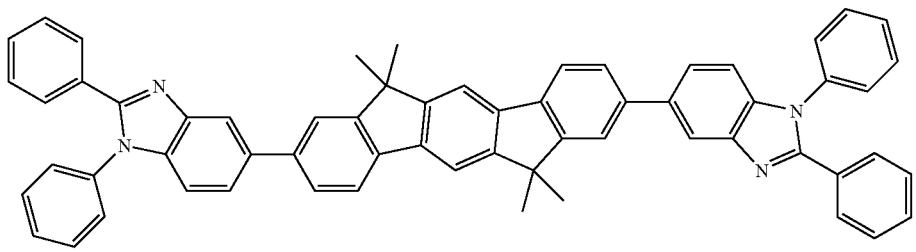

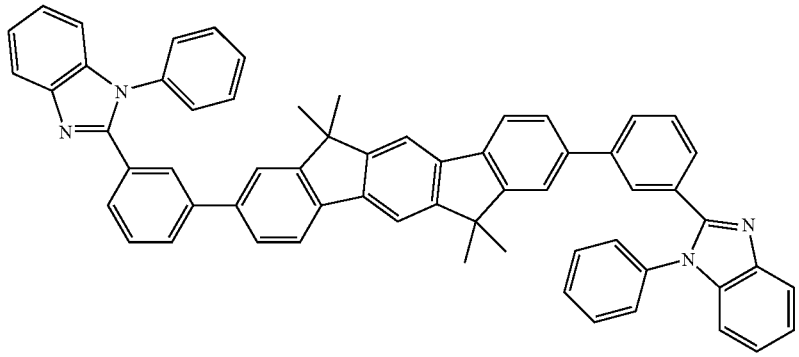

-continued
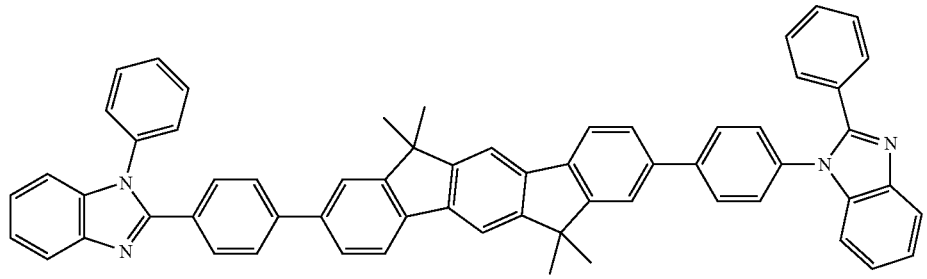
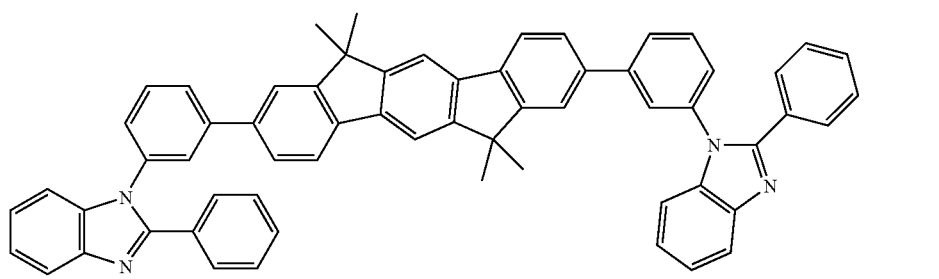
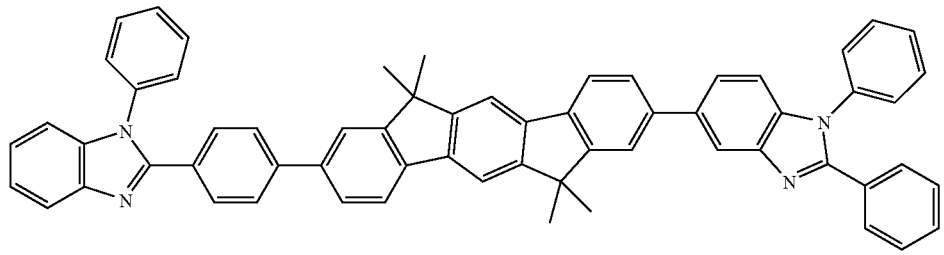
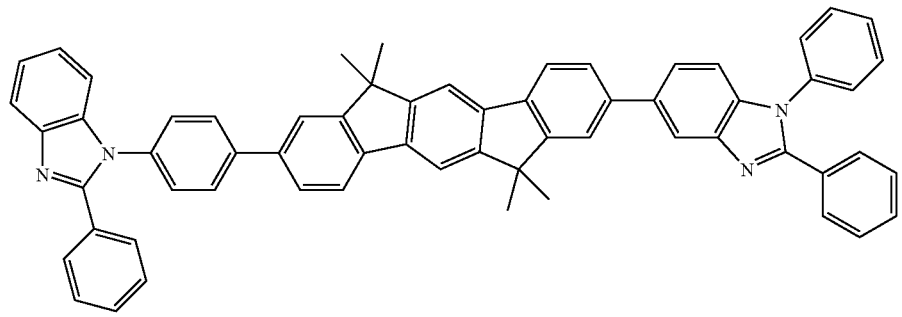
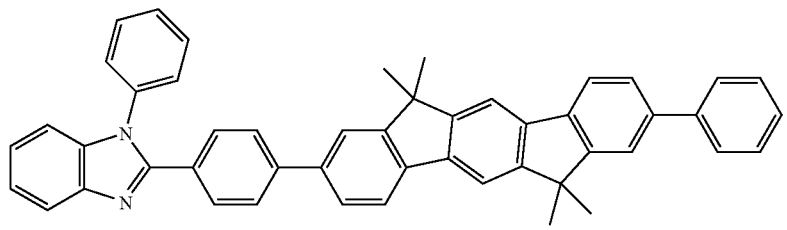
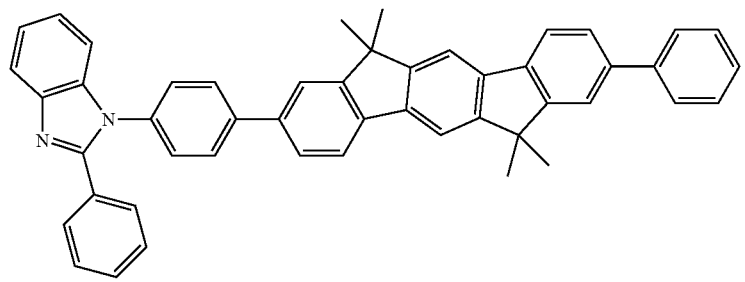

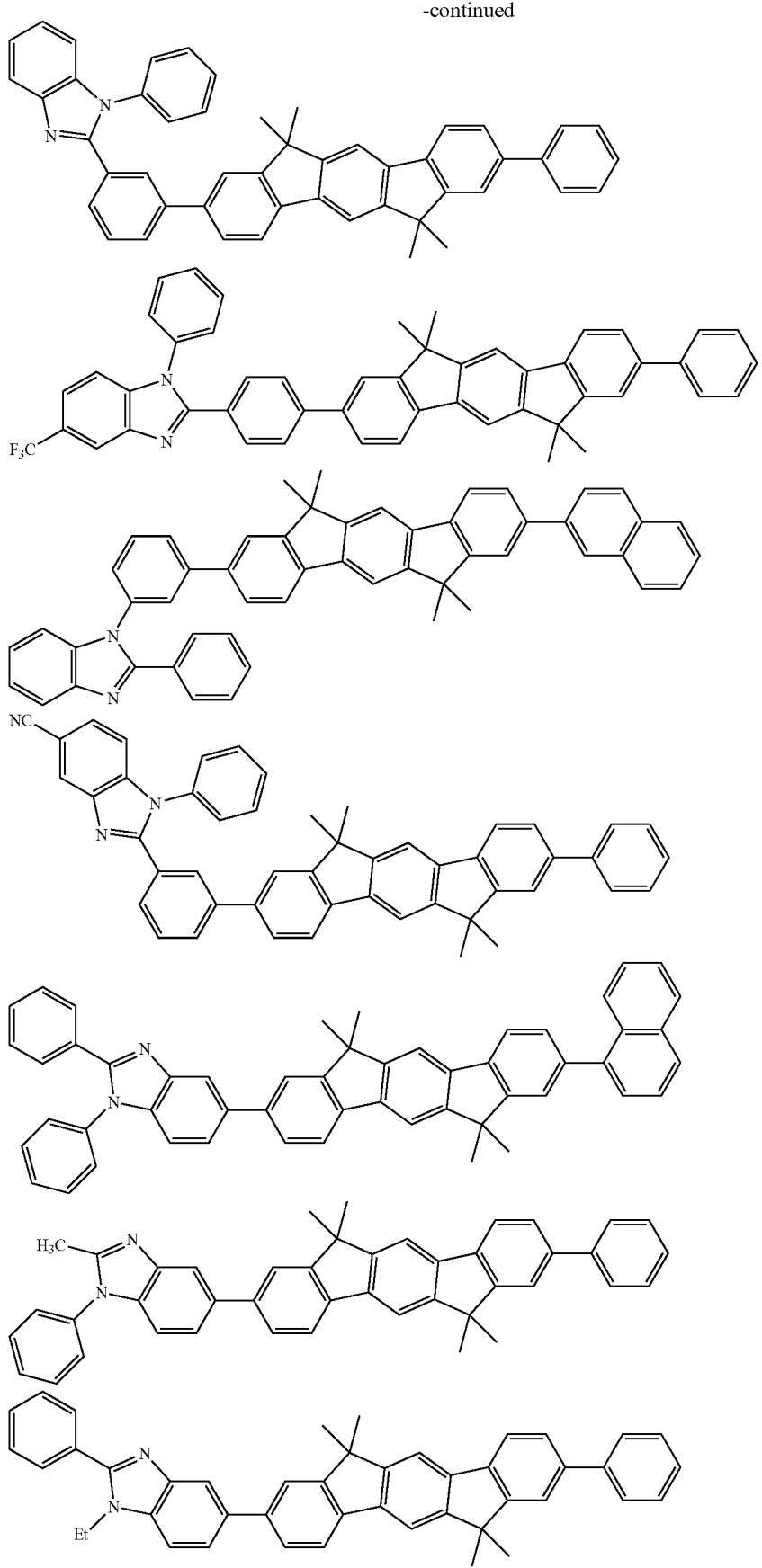

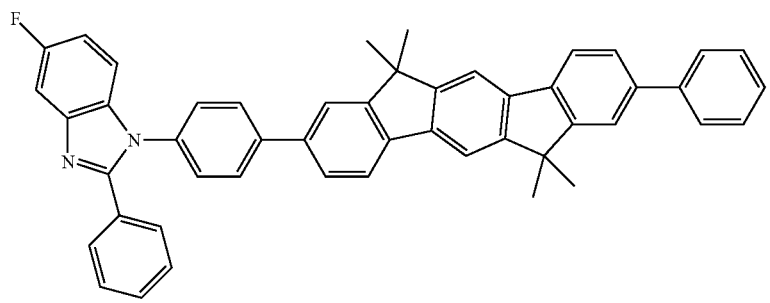
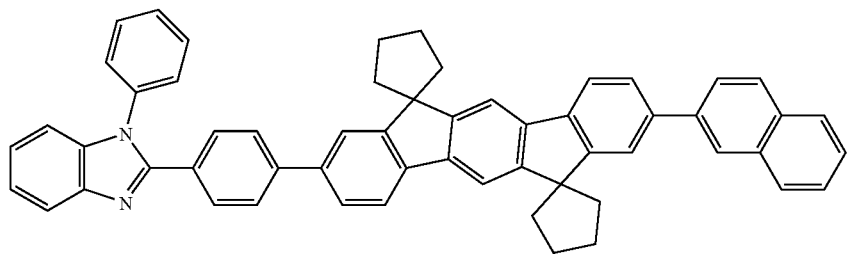
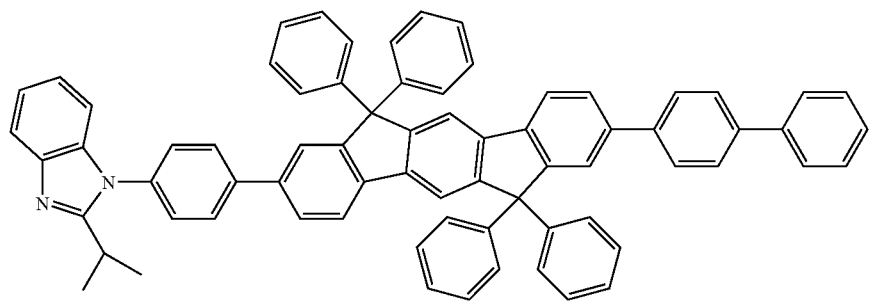
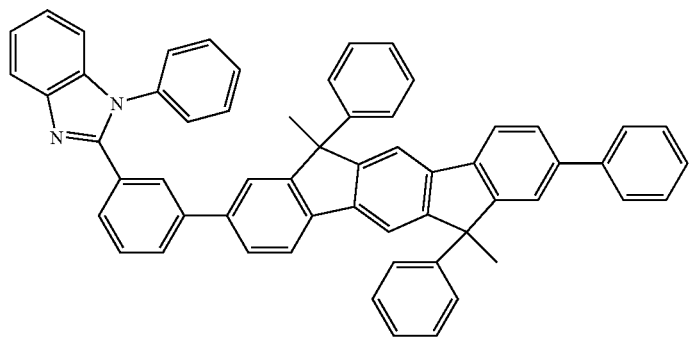
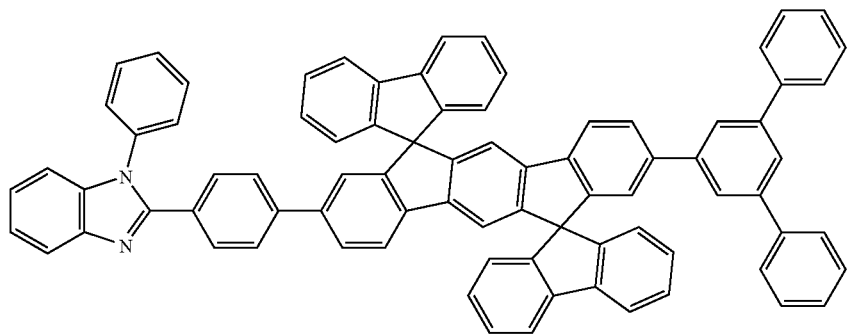

-continued
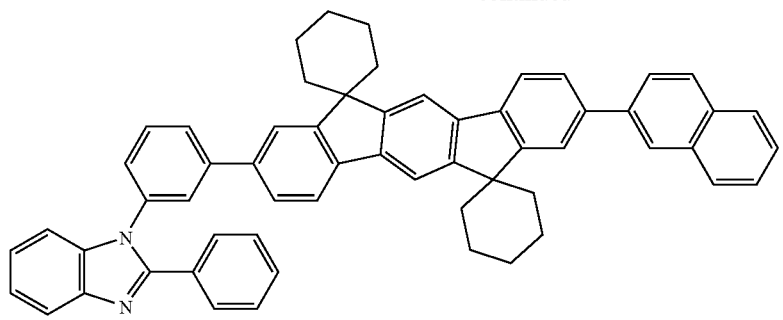
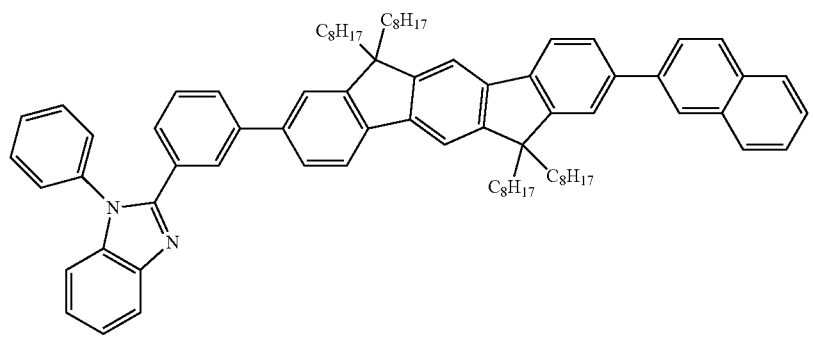
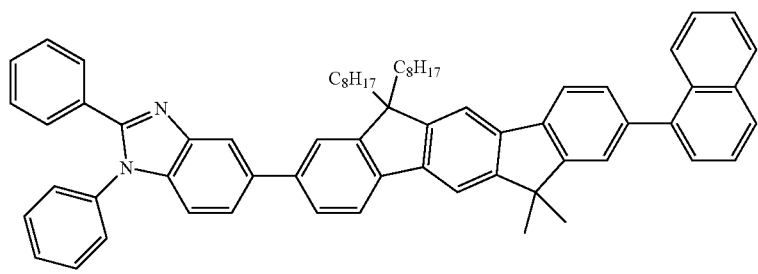
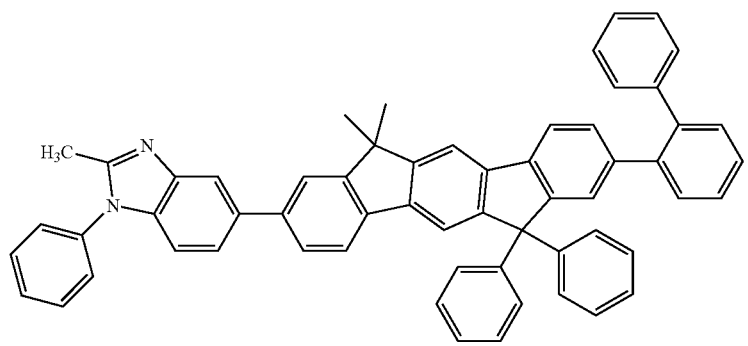
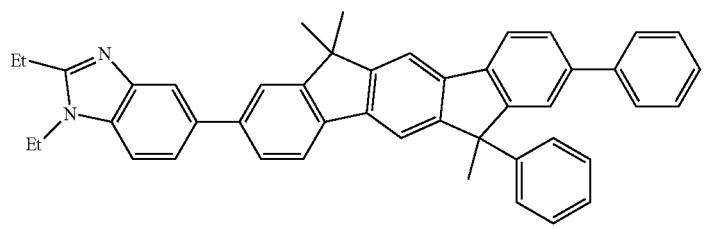

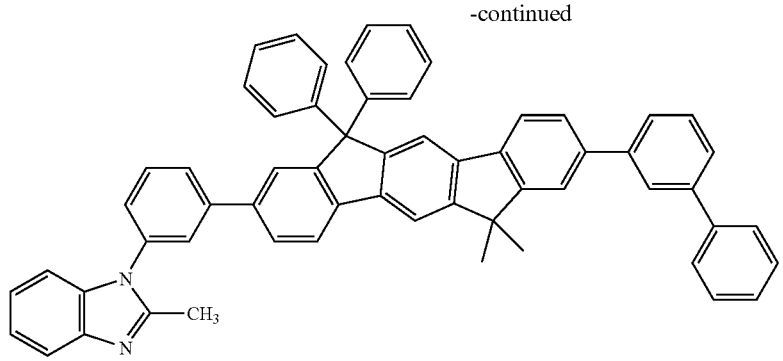
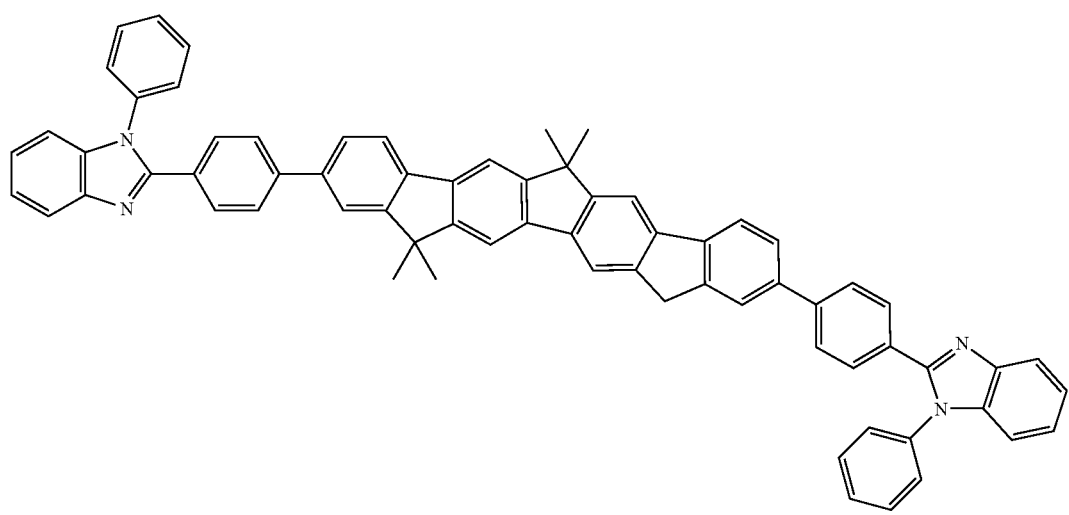
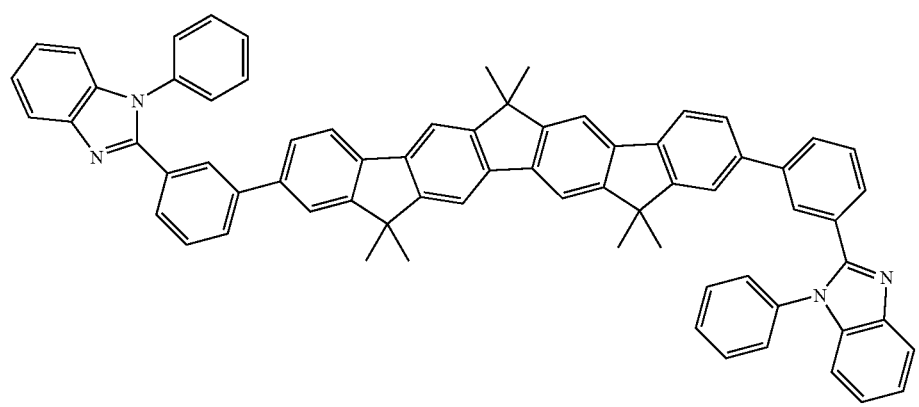
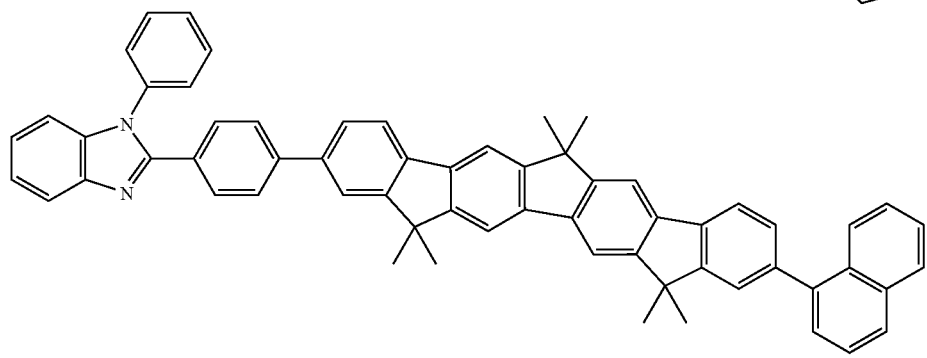

-continued

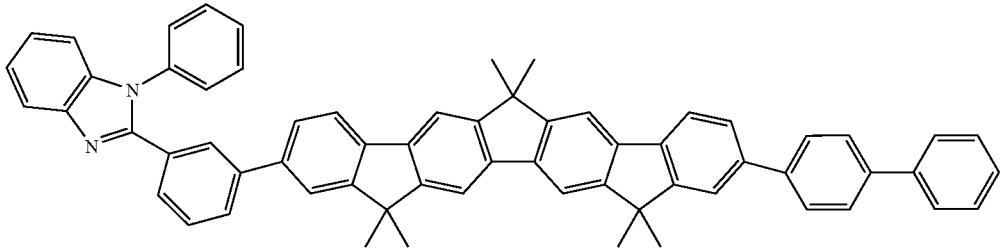

The organic EL device of the present invention will be described in the following.

The organic EL device of the present invention comprises an anode, a cathode and an organic thin film layer which comprises a single layer or a plurality of layers comprising at least a light emitting layer and is disposed between the anode and the cathode, wherein at least one layer in the organic thin film layer comprises the nitrogen-containing heterocyclic derivative described above singly or as a component of a mixture.

In the organic EL device of the present invention, it is preferable that the organic thin film layer comprises an electron injecting and transporting layer, and the electron injecting and transporting layer comprises the nitrogen-containing heterocyclic derivative of the present invention singly or as a component of a mixture. It is more preferable that the electron injecting and transporting layer comprises the nitrogen-containing heterocyclic derivative as the main component thereof.

The construction of the organic EL device of the present invention will be described in the following.

(1) Construction of the Organic EL Device

Typical examples of the construction of the organic EL device include:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to those shown above as the examples.

The nitrogen-containing heterocyclic derivative of the present invention may be used for any layer in the organic thin film layer. It is preferable that the nitrogen-containing heterocyclic derivative is used for the light emitting zone or the electron transporting zone and more preferably for the electron injecting layer, the electron transporting layer or the light emitting layer.

(2) Substrate Transmitting Light

The organic EL device of the present invention is prepared on a substrate transmitting light. The substrate transmitting light is the substrate supporting the organic EL device. It is preferable that the substrate transmitting light is flat and smooth and has a transmittance of light of 50% or greater in the visible region of 400 to 700 nm.

Examples of the substrate transmitting light include glass plates and polymer plates. Examples of the glass plate include plates made of soda-lime glass, glass containing barium and strontium, lead glass, aluminosilicate glass, borosilicate glass, barium borosilicate glass and quartz. Examples of the polymer plate include plates made of polycarbonates, acrylic resins, polyethylene terephthalate, polyether sulfides and polysulfones.

(3) Anode

The anode in the organic EL device of the present invention has the function of injecting holes into the hole transporting layer or the light emitting layer. It is effective that the anode has a work function of 4.5 eV or greater. Examples of the material for the anode used in the present invention include indium tin oxide alloys (ITO), tin oxide (NESA), indium zinc oxide (IZO), gold, silver, platinum and copper.

The anode can be prepared by forming a thin film of the electrode substance described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm although the range may be different depending on the used material.

(4) Light Emitting Layer

The light emitting layer in the organic EL device has the combination of the following functions (1) to (3):

(1) The injecting function: the function of injecting holes from the anode or the hole injecting layer and injecting electrons from the cathode or the electron injecting layer when an electric field is applied;
(2) The transporting function: the function of transporting injected charges (electrons and holes) by the force of the electric field; and (3) The light emitting function: the function of providing the field for recombination of electrons and holes and leading the recombination to the emission of light.

The easiness of the hole injection and the easiness of the electron injection may be different from each other. The abilities of transportation of holes and electrons expressed by the mobilities of holes and electrons, respectively, may be different from each other. It is preferable that one of the charges is transported.

As the process for forming the light emitting layer, a conventional process such as the vapor deposition process, the spin coating process and the LB process can be used. It is particularly preferable that the light emitting layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in aggregation structures and higher order structures and the functional differences caused by these structural differences.

As disclosed in Japanese Patent Application Laid-Open No. Showa 57 (1982)-51781, the light emitting layer can also be formed by dissolving a binder such as a resin and the material compounds into a solvent to prepare a solution, followed by forming a thin film from the prepared solution in accordance with the spin coating process or the like.

In the organic EL device of the present invention, where desired, the light emitting layer may further comprise conventional light emitting materials other than the light emitting material comprising the nitrogen-containing heterocyclic derivative of the present invention or a light emitting layer comprising conventional light emitting materials may be laminated to the light emitting layer comprising the light emitting material comprising the nitrogen-containing heterocyclic derivative of the present invention as long as the object of the present invention is not adversely affected.

In the organic EL device of the present invention, it is preferable that the light emitting layer comprises an arylamine compound and/or a styrylamine compound.

Examples of the arylamine compound include compounds represented by the following general formula (A). Examples of the styrylamine compound include compounds represented by the following general formula (B).

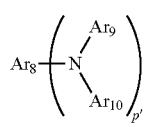

(A)

In general formula (A), $Ar_8$ represents a group selected from phenyl group, biphenyl group, terphenyl group, stilbene group and distyrylaryl groups, and $Ar_9$ and $Ar_{10}$ each represent hydrogen atom or an aromatic group having 6 to 20 carbon atoms. The groups represented by $Ar_9$ and $Ar_{10}$ may be substituted. p' represents an integer of 1 to 4. It is preferable that at least one of the groups represented by $Ar_9$ and $Ar_{10}$ is substituted with styryl group.

As the aromatic group having 6 to 20 carbon atoms, phenyl group, naphthyl group, anthryl group, phenanthryl group and terphenyl group are preferable.

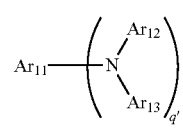

(B)

In general formula (B), $Ar_{11}$ to $Ar_{13}$ each represent an aryl group having 5 to 40 ring carbon atoms which may be substituted, and q' represents an integer of 1 to 4.

As the aryl group having 5 to 40 ring atoms, phenyl group, naphthyl group, anthryl group, phenanthryl group, pyrenyl group, coronyl group, biphenyl group, terphenyl group, pyrrolyl group, furanyl group, thiophenyl group, benzothiophenyl group, oxadiazolyl group, diphenylanthryl group, indolyl group, carbazolyl group, pyridyl group, benzoquinolyl group, fluoranthenyl group, acenaphthofluoranthenyl group and stilbene group are preferable. The aryl group having 5 to 40 ring atoms may be further substituted with a substituent. Preferable examples of the substituent include alkyl groups having 1 to 6 carbon atoms (such as ethyl group, methyl group, isopropyl group, n-propyl group, s-butyl group, t-butyl group, pentyl group, hexyl group, cyclopentyl group and cyclohexyl group), alkoxy groups having 1 to 6 carbon atoms (such as ethoxy group, methoxy group, isopropoxy group, n-propoxy group, s-butoxy group, t-butoxy group, pentoxy group, hexyloxy group, cyclopentoxy group and cyclohexyloxy group), aryl groups having 5 to 40 ring atoms, amino groups substituted with an aryl group having 5 to 40 ring atoms, ester groups having an aryl group having 5 to 40 ring atoms, ester groups having an alkyl group having 1 to 6 carbon atoms, cyano group, nitro group and halogen atoms (such as chorine atom, bromine atom and iodine atom).

Examples of the light emitting material and the doping material which can be used in the light emitting layer include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenyl-butadiene, coumarine, oxadiazole, aldazine, bisbenzoxazoline, bisstyryl, pyrazine, cyclopentadiene, metal complex compounds of quinoline, metal complex compounds of aminoquinoline, metal complex compounds of benzoquinoline, imines, diphenylethylene, vinylanthracene, diamino-carbazole, pyrane, thiopyrane, polymethine, melocyanine, oxinoid compounds chelated with imidazole, quinacridone, rubrene and fluorescent coloring agents. However, the light emitting material and the doping material are not limited to the above compounds.

As the host material which can be used in the light emitting layer, compounds represented by the following general formulae (i) to (ix) are preferable.

Asymmetric anthracenes represented by the following general formula (i):

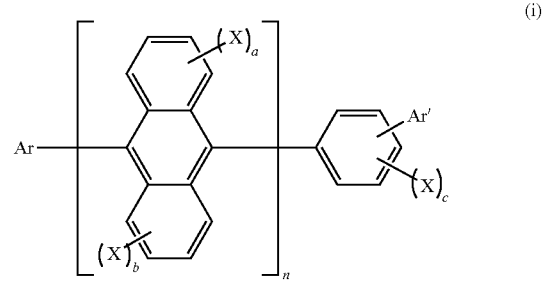

(i)

In the above general formula, Ar represents a substituted or unsubstituted condensed aromatic group having 10 to 50 ring carbon atoms.

Ar' represents a substituted or unsubstituted aromatic group having 6 to 50 ring carbon atoms.

X represents a substituted or unsubstituted aromatic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, carboxy group, a halogen atom, cyano group, nitro group or hydroxy group.

a, b and c each represent an integer of 0 to 4.

n represents an integer of 1 to 3. When n represents an integer of 2 or greater, a plurality of groups shown in [ ] may be the same with or different from each other.

Asymmetric monoanthracene derivatives represented by the following general formula (ii):

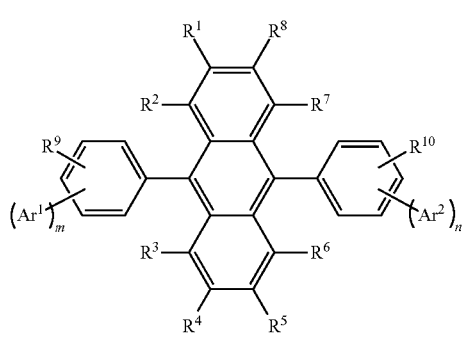

(ii)

In the above general formula, $Ar^1$ and $Ar^2$ each independently represent a substituted or unsubstituted aromatic cyclic group having 6 to 50 ring carbon atoms, and m and n each represents an integer of 1 to 4. When m=n=1 and the positions of bonding of the groups represented by $Ar^1$ and $Ar^2$ to the benzene rings at the left side and at the right side, respectively, are symmetric, $Ar^1$ and $Ar^2$ do not represent the same group. When m or n represents an integer of 2 to 4, m and n represent integers different from each other.

$R^1$ to $R^{10}$ each independently represent hydrogen atom, a substituted or unsubstituted aromatic cyclic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, carboxy group, a halogen atom, cyano group, nitro group or hydroxy group.

Asymmetric pyrene derivatives represented by the following general formula (iii):

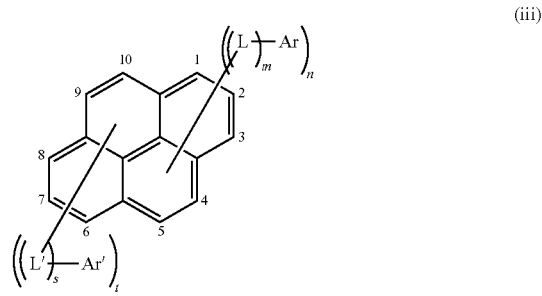

(iii)

In the above general formula, Ar and Ar' each represent a substituted or unsubstituted aromatic group having 6 to 50 ring carbon atoms.

L and L' each represent a substituted or unsubstituted phenylene group, a substituted or unsubstituted naphthalenylene group, a substituted or unsubstituted fluorenylene group or a substituted or unsubstituted dibenzosilolylene group.

m represents an integer of 0 to 2, n represents an integer of 1 to 4, s represents an integer of 0 to 2, and t represents an integer of 0 to 4.

The group represented by L or Ar is bonded at one of 1 to 5 positions of pyrene, and the group represented by L' or Ar' is bonded at one of 6 to 10 positions of pyrene.

When n+t represents an even number, the groups represented by Ar, Ar', L and L' satisfy the following condition (1) or (2):

(1) Ar≠Ar' and/or L≠L' (≠ means the groups have structures different from each other)

(2) When Ar=Ar' and L=L',
(2-1) m≠s and/or n≠t, or
(2-2) When m=s and n=t,
the case where the positions of substitution of L and L' or Ar and Ar' on pyrene are the 1-position and the 6-position, respectively, or the 2-position and the 7-position, respectively, is excluded when
(2-2-1) L and L' or pyrene are bonded at different bonding positions on Ar and Ar', respectively, or
(2-2-2) L and L' or pyrene are bonded at the same bonding position on Ar and Ar', respectively.

Asymmetric anthracene derivatives represented by the following general formula (iv):

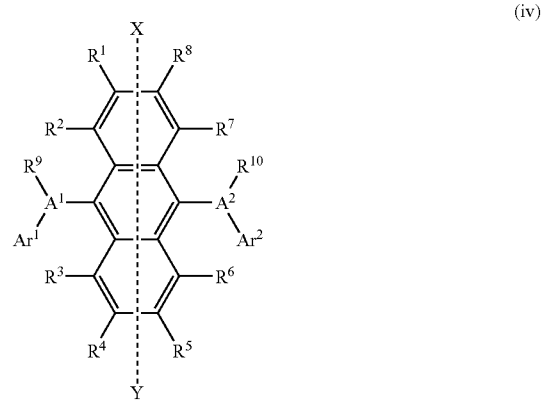

(iv)

In the above general formula, $A^1$ and $A^2$ each independently represent a substituted or unsubstituted condensed aromatic cyclic group 5 having 10 to 20 ring carbon atoms.

$Ar^1$ and $Ar^2$ each independently represent hydrogen atom or a substituted or unsubstituted aromatic cyclic group having 6 to 50 ring carbon atoms.

$R^1$ to $R^{10}$ each independently represent hydrogen atom, a substituted or unsubstituted aromatic cyclic group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, carboxy group, a halogen atom, cyano group, nitro group or hydroxy group.

$Ar^1$, $Ar^2$, $R^9$ and $R^{10}$ may each be present in plurality. Adjacent atoms and groups among the atoms and the groups represented by $Ar^1$, $Ar^2$, $R^9$ and $R^{10}$ may be bonded to each other to form a saturated or unsaturated cyclic structure.

The case where the groups are bonded to the 9- and 10-positions of anthracene in general formula (iv) to form a symmetric structure with respect to line X-Y shown on the anthracene structure is excluded.

Anthracene derivatives represented by the following general formula (v):

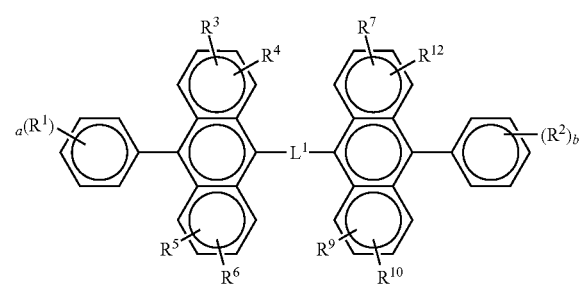

(v)

In the above general formula, $R^1$ to $R^{10}$ each independently represent hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted. a and b each represent an integer of 1 to 5. When a or b represents an integer of 2 or greater, the atoms and the groups represented by a plurality of $R^1$ or by a plurality of $R^2$, respectively, may be the same with or different from each other or may be bonded to each other to form a ring. The atoms and the groups represented by the pair of $R^3$ and $R^4$, $R^5$ and $R^6$, $R^7$ and $R^8$ or $R^9$ and $R^{10}$ may be bonded to each other to form a ring. $L^1$ represents the single bond, —O—, —S—. —N(R)— (wherein R representing an alkyl group or an aryl group which may be substituted), an alkylene group or an arylene group.

Anthracene derivatives represented by the following general formula (vi):

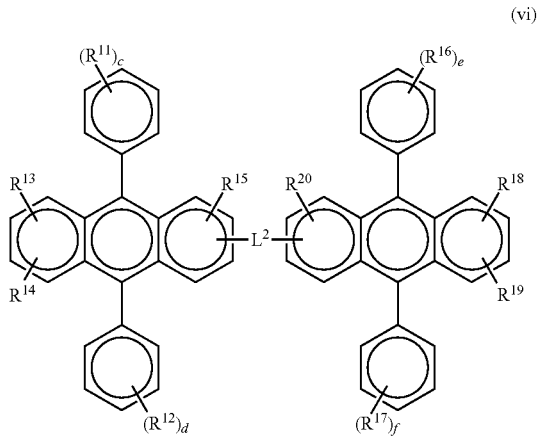

(vi)

In the above general formula, $R^{11}$ to $R^{20}$ each independently represent hydrogen atom, an alkyl group, a cycloalkyl group, an aryl group, an alkoxy group, an aryloxy group, an alkylamino group, an arylamino group or a heterocyclic group which may be substituted. c, d, e and f each represent an integer of 1 to 5. When c, d, e or f represents an integer of 2 or greater, the atoms and the groups represented by the plurality of $R^{11}$, by the plurality of $R^{12}$, by the plurality of $R^{16}$ or by the plurality of $R^{17}$, respectively, may be the same with or different from each other or may be bonded to each other to form a ring. The atoms and the groups represented by the pair of $R^{13}$ and $R^{14}$ or the pair of $R^{18}$ and $R^{19}$ may be bonded to each other to form a ring. $L^2$ represents the single bond, —O—, —S—. —N(R)— (wherein R representing an alkyl group or an aryl group which may be substituted), an alkylene group or an arylene group.

Spirofluorene derivatives represented by the following general formula (vii):

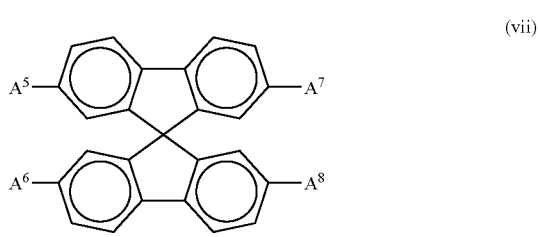

(vii)

In the above general formula, $A^5$ to $A^8$ each independently represent substituted or unsubstituted biphenyl group or substituted or unsubstituted naphthyl group.

Compounds having a condensed ring represented by the following general formula (viii):

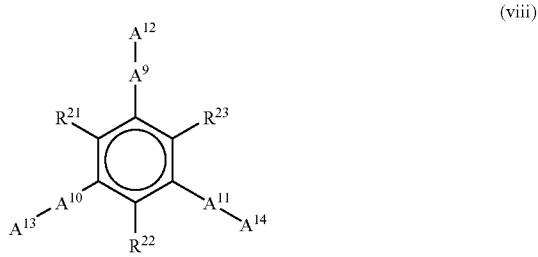

(viii)

In the above general formula, $A^9$ to $A^{14}$ are as defined above. $R^{21}$ to $R^{23}$ each independently represent hydrogen atom, an alkyl group having 1 to 6 carbon atoms, a cycloalkyl group having 3 to 6 carbon atoms, an alkoxy group having 1 to 6 carbon atoms, an aryloxy group having 5 to 18 carbon atoms, an aralkyloxy group having 7 to 18 carbon atoms, an arylamino group having 5 to 16 carbon atoms, nitro group, cyano group, an ester group having 1 to 6 carbon atoms or a halogen atom. At least one of $A^9$ to $A^{14}$ represents a group having condensed aromatic rings having 3 or more rings.

Fluorene compounds represented by the following general formula (ix):

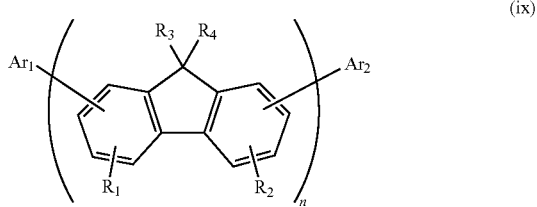

In the above general formula, $R_1$ and $R_2$ each represent hydrogen atom, a substituted or unsubstituted alkyl group, a substituted or unsubstituted aralkyl group, a substituted or unsubstituted aryl group, a substituted or unsubstituted heterocyclic group, a substituted amino group, cyano group or a halogen atom. The atoms and the groups represented by a plurality of $R_1$ or by a plurality of $R_2$ each bonded to different fluorene groups may be the same with or different from each other. The atoms and the groups represented by $R_1$ and $R_2$ each bonded to the same fluorene group may be the same with or different from each other. $R_3$ and $R_4$ each represent hydrogen atom, a substituted or unsubstituted alkyl group, a substituted or unsubstituted aralkyl group, a substituted or unsubstituted aryl group or a substituted or unsubstituted heterocyclic group. The atoms and the groups represented by a plurality of $R_3$ or by a plurality of $R_4$ each bonded to different fluorene groups may be the same with or different from each other. The atoms and the groups represented by $R_3$ and $R_4$ each bonded to the same fluorene group may be the same with or different from each other. $Ar_1$ and $Ar_2$ each represent a substituted or unsubstituted condensed polycyclic aromatic group having 3 or more benzene rings as the total or a substituted or unsubstituted polycyclic heterocyclic group having 3 or more rings as the total of the benzene ring and heterocyclic rings which is bonded to fluorene group via carbon atom. The groups represented by $Ar^1$ and $Ar^2$ may be the same with or different from each other. n represents an integer of 1 to 10.

Among the above host materials, the anthracene derivatives are preferable, the monoanthracene derivatives are more preferable, and the asymmetric anthracene derivatives are most preferable.

As the light emitting material of the dopant, a compound emitting phosphorescent light may be used.

As the compound emitting phosphorescent light, a compound having carbazole ring is preferable for the host material. The dopant is a compound which can emit light from the triplet exciton. The dopant is not particularly limited as long as light is emitted from the triplet exciton. Metal complex compounds having at least one metal selected from the group of Ir, Ru, Pd, Pt, Os and Re are preferable, and porphyrin metal complex compounds and ortho-metalated complex compounds are more preferable.

The host compound comprising a compound having carbazole ring, which is advantageously used for the emission of phosphorescent light, is a compound exhibiting the function of inducing a compound emitting phosphorescent light to emit light as the result of energy transfer from the host compound in the excited state to the compound emitting phosphorescent light. The host compound is not limited as long as the energy of the exciton can be transferred to the compound emitting phosphorescent light and can be suitably selected in accordance with the object. The host compound may have a desired heterocycle other than carbazole ring.

Examples of the host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, chalcone derivatives substituted with an amino group, styrylanthracene derivatives, fluorenone derivatives, hydrazone derivatives, stilbene derivatives, silazane derivatives, aromatic tertiary amine compounds, styrylamine compounds, aromatic dimethylidine-based compounds, porphyrin-based compounds, anthraquinodimethane derivatives, anthrone derivatives, diphenylquinone derivatives, thiopyrane dioxide derivatives, carbodiimide derivatives, fluorenylidenemethane derivatives, distyrylpyrazine derivatives, anhydrides of heterocyclic tetracarboxylic acids derived from naphthalene, perylene and the like, phthalocyanine derivatives, metal complex compounds of 8-quinolinol derivatives, metal phthalocyanines, metal complex compounds using benzoxazole and benzothiazole as ligands, polysilane-based compounds, electrically conductive macromolecular oligomers such as poly(N-vinylcarbazole) derivatives, aniline-based copolymer, thiophene oligomers and polythiophene and macromolecular compounds such as polythiophene derivatives, polyphenylene derivatives, polyphenylene vinylene derivatives and polyfluorene derivatives. The host compound may be used singly or in combination of two or more.

Examples of the host compound include the compounds shown in the following:

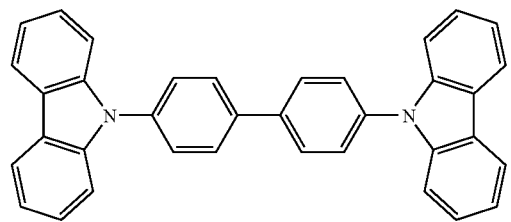

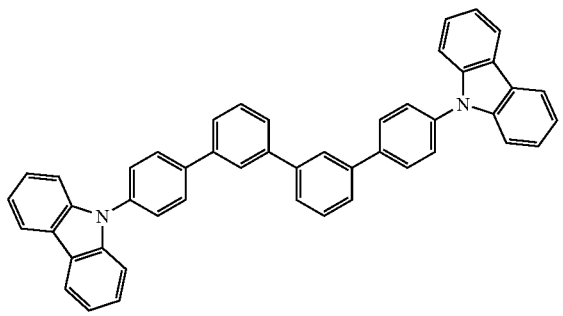

-continued

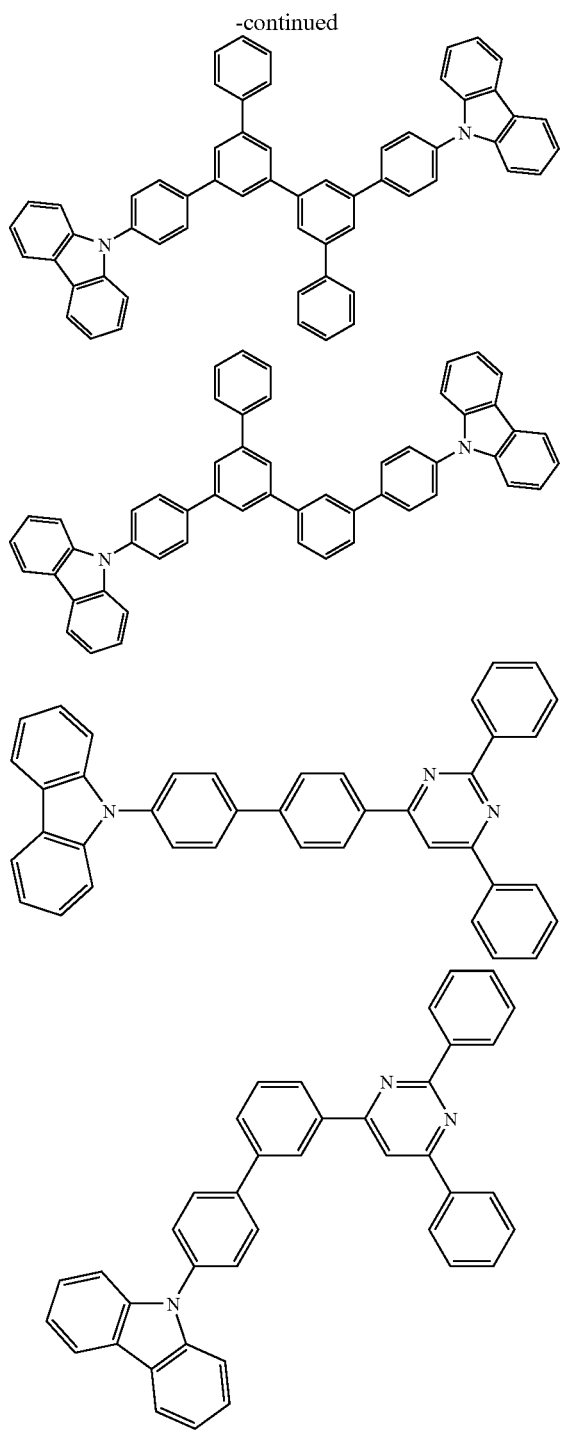

The dopant emitting phosphorescent light is a compound which can emit light from the triplet exciton. The dopant is not limited as long as light is emitted from the triplet exciton. Metal complex compounds having at least one metal selected from the group of Ir, Ru, Pd, Pt, Os and Re are preferable, and porphyrin metal complex compounds and ortho-metalated complex compounds are more preferable. As the porphyrin metal complex compound, porphyrin platinum complex compounds are preferable. The compound emitting phosphorescent light may be used singly or in combination of two or more.

As the ligand forming the ortho-metalated complex compound, various ligands can be used. Examples of the preferable ligand include 2-phenylpyridine derivatives, 7,8-benzoquinoline derivatives, 2-(2-thienyl)pyridine derivatives, 2-(1-naphthyl)pyridine derivatives and 2-phenylquinoline derivatives. These derivatives may have substituents, where necessary. In particular, fluorides and ligands having trifluoromethyl group are preferable for the dopant emitting bluish light. Ligands other than those described above such as acetyl acetonates and picric acid may be present as the auxiliary ligand.

The content of the dopant emitting phosphorescent light in the light emitting layer is not particularly limited and can be suitably selected in accordance with the object. The content is, for example, 0.1 to 70% by mass and preferably 1 to 30% by mass. When the content of the compound emitting phosphorescent light is smaller than 0.1% by mass, the light emission is weak, and the effect of using the dopant is not exhibited. When the content exceeds 70% by mass, the phenomenon called concentration quenching arises markedly, and the property of the device deteriorates.

The light emitting layer may further comprise a hole transporting material, an electron transporting material and a polymer binder, where necessary.

The thickness of the light emitting layer is preferably 5 to 50 nm, more preferably 7 to 50 nm and most preferably 10 to 50 nm. When the thickness is smaller than 5 nm, the formation of the light emitting layer becomes difficult, and there is the possibility that the adjustment of the chromaticity becomes difficult. When the thickness exceeds 50 nm, there is the possibility that the driving voltage increases.

(5) Hole Injecting and Transporting Layer (Hole Transporting Zone)

The hole injecting and transporting layer is a layer which helps injection of holes into the light emitting layer and transports the holes to the light emitting region. The layer exhibits a great mobility of holes and, in general, has an ionization energy as small as 5.5 eV or smaller. For the hole injecting and transporting layer, a material which transports holes to the light emitting layer under an electric field of a smaller strength is preferable. A material which exhibits, for example, a mobility of holes of at least $10^{-4}$ cm$^2$/V·second under application of an electric field of $10^4$ to $10^6$ V/cm is preferable.

Examples include triazole derivatives (U.S. Pat. No. 3,112, 197), oxadiazole derivatives (U.S. Pat. No. 3,189,447), imidazole derivatives (Japanese Patent Application Publication No. Showa 37 (1962)-16096), polyarylalkane derivatives (U.S. Pat. Nos. 3,615,402, 3,820,989 and 3,542,544; Japanese Patent Application Publication Nos. Showa 45 (1970)-555 and Showa 51 (1976)-10983; and Japanese Patent Application Laid-Open Nos. Showa 51 (1976)-93224, Showa 55 (1980)-17105, Showa 56 (1981)-4148, Showa 55 (1980)-108667, Showa 55 (1980)-156953 and Showa 56 (1981)-36656); pyrazoline derivatives and pyrazolone derivatives (U.S. Pat. Nos. 3,180,729 and 4,278,746; and Japanese Patent Application Laid-Open Nos. Showa 55 (1980)-88064, Showa 55 (1980)-88065, Showa 49 (1974)-105537, Showa 55 (1980)-51086, Showa 56 (1981)-80051, Showa 56 (1981)-88141, Showa 57 (1982)-45545, Showa 54 (1979)-112637 and Showa 55 (1980)-74546); phenylenediamine derivatives (U.S. Pat. No. 3,615,404; Japanese Patent Application Publication Nos. Showa 51 (1976)-10105, Showa 46 (1971)-3712 and Showa 47 (1972)-25336; and Japanese Patent Application Laid-Open No. Showa 54 (1979)-119925); arylamine derivatives (U.S. Pat. Nos. 3,567,450, 3,240,597, 3,658,520, 4,232,103, 4,175,961 and 4,012,376; Japanese Patent Application Publication Nos. Showa 49 (1974)-35702 and Showa 39 (1964)-27577; Japanese Patent Application Laid-Open Nos. Showa 55 (1980)-144250, Showa 56 (1981)-119132 and Showa 56 (1981)-22437; and West German Patent No. 1,110, 518); chalcone derivatives substituted with amino group (U.S. Pat. No. 3,526,501); oxazole derivatives (U.S. Pat. No. 3,257,203); styrylanthracene derivatives (Japanese Patent Application Laid-Open Nos. Showa 56 (1981)-46234); fluorenone derivatives (Japanese Patent Application Laid-Open Nos. Showa 54 (1979)-110837); hydrazone derivatives (U.S. Pat. No. 3,717,462; and Japanese Patent Application Laid-Open Nos. Showa 54 (1979)-59143, Showa 55 (1980)-52063, Showa 55 (1980)-52064, Showa 55 (1980)-46760, Showa 57 (1982)-11350, Showa 57 (1982)-148749 and Heisei 2 (1990)-311591); stilbene derivatives (Japanese Patent Application Laid-Open Nos. Showa 61 (1986)-210363, Showa 61 (1986)-228451, Showa 61 (1986)-14642, Showa 61 (1986)-72255, Showa 62 (1987)-47646, Showa 62 (1987)-36674, Showa 62 (1987)-10652, Showa 62 (1987)-30255, Showa 60 (1985)-93455, Showa 60 (1985)-94462, Showa 60 (1985)-174749 and Showa 60 (1985)-175052); silazane derivatives (U.S. Pat. No. 4,950,950); polysilane-based compounds (Japanese Patent Application Laid-Open No. Heisei 2 (1990)-204996); aniline-based copolymers (Japanese Patent Application Laid-Open No. Heisei 2 (1990)-282263); and electrically conductive macromolecular oligomers (in particular, thiophene oligomers).

Besides the above materials which can be used as the material for the hole injecting and transporting layer, porphyrin compounds (compounds disclosed in Japanese Patent Application Laid-Open No. Showa 63 (1988)-2956965); and aromatic tertiary amine compounds and styrylamine compounds (U.S. Pat. No. 4,127,412 and Japanese Patent Application Laid-Open Nos. Showa 53 (1978)-27033, Showa 54 (1979)-58445, Showa 55 (1980)-79450. Showa 55 (1980)-144250, Showa 56 (1981)-119132, Showa 61 (1986)-295558, Showa 61 (1986)-98353 and Showa 63 (1988)-295695) are preferable, and the aromatic tertiary amines are more preferable.

Further examples include compounds having two condensed aromatic rings in the molecule which are described in the U.S. Pat. No. 5,061,569 such as 4,4'-bis(N-(1-naphthyl)-N-phenylamino)-biphenyl (referred to as NPD, hereinafter) and a compound in which three triphenylamine units are bonded together in a star-burst shape, which is described in Japanese Patent Application Laid-Open No. Heisei 4 (1992)-308688, such as 4,4',4''-tris(N-(3-methylphenyl)-N-phenylamino)-triphenylamine (referred to as MTDATA, hereinafter).

Besides the aromatic dimethylidine-based compounds shown above as the examples of the material for the light emitting layer, inorganic compounds such as Si of the p-type and SiC of the p-type can also be used as the material for the hole injecting and transporting layer.

The hole injecting and transporting layer can be formed by preparing a thin film of the material described above in accordance with a conventional process such as the vacuum vapor deposition process, the spin coating process, the casting process and the LB process. The thickness of the hole injecting and transporting layer is not particularly limited. In general, the thickness is 5 nm to 5 µm. The hole injecting and transporting layer may be constituted with a single layer comprising one or more types of the materials described above or with a laminate of the hole injecting and transporting layer described above and a hole injecting and transporting layer comprising other compounds.

An organic semiconductor layer may be disposed as a layer helping injection of holes or electrons into the light emitting layer. As the organic semiconductor layer, a layer having a conductivity of $10^{-10}$ S/cm or greater is preferable. As the material for the organic semiconductor layer, conductive oligomers such as oligomers containing thiophene and oligomers containing arylamines disclosed in Japanese Patent Application Laid-Open No. Heisei 8 (1996)-193191 and conductive dendrimers such as dendrimers containing arylamines, can also be used.

(6) Electron Injecting and Transporting Layer

The electron injecting and transporting layer is a layer which helps injection of electrons into the light emitting layer and transportation of the electrons to the light emitting region. The electron injecting and transporting layer exhibits a great mobility of electrons. The adhesion improving layer is an electron injecting layer comprising a material exhibiting improved adhesion, in particular, with the cathode. In the organic EL device of the present invention, it is preferable that the above compound of the present invention is used for the electron injecting layer, the electron transporting layer and the adhesion improving layer.

When the nitrogen-containing heterocyclic derivative of the present invention is used for the electron transporting zone, the nitrogen-containing heterocyclic derivative of the present invention may be used for forming the electron injecting and transporting layer singly or as a mixture or a laminate with other materials.

The material used for forming the electron injecting and transporting layer as a mixture or a laminate with the nitrogen-containing heterocyclic derivative of the present invention is not limited as long as the material has the preferable properties described above and can be selected as desired from materials conventionally used as the charge transporting material of electrons in photoconductive materials and materials used for the electron injecting and transporting layer of organic EL devices.

A device comprising a reducing dopant in the region transporting electrons or in the interfacial region between the cathode and the organic layer is preferable as an embodiment of the organic EL device of the present invention. In the present invention, an organic EL device which comprises a reducing dopant in the compound of the present invention is preferable. The reducing dopant is defined as a substance which can reduce a compound having the electron transporting property. Various compounds can be used as the reducing dopant as long as the compounds have the specific reductive property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complex compounds of alkali metals, organic complex compounds of alkaline earth metals and organic complex compounds of rare earth metals can be advantageously used.

Preferable examples of the reducing dopant include substances having a work function of 2.9 eV or smaller, specific examples of which include at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV). Among the above substances, at least one alkali metal selected from the group consisting of K, Rb and Cs is more preferable, Rb and Cs are still more preferable, and Cs is most preferable as the reducing dopant. These alkali metals have great reducing ability, and the luminance of the emitted light and the life of the organic EL device can be increased by addition of a relatively small amount of the alkali metal into the electron injecting zone. As the reducing dopant having a work function of 2.9 eV or smaller, combinations of two or more alkali metals are also preferable. Combinations having Cs such as the combinations of Cs and Na, Cs and K, Cs and Rb and Cs, Na and K are more preferable. The reducing ability can be efficiently exhibited by the combination having Cs. The luminance of emitted light and the life of the organic EL device can be increased by adding the combination having Cs into the electron injecting zone.

In the present invention, an electron injecting layer which is constituted with an insulating material or a semiconductor may further be disposed between the cathode and the organic layer. By disposing the above electron injecting layer, leak of electric current can be effectively prevented, and the electron injecting property can be improved. As the insulating material, at least one metal compound selected from the group consisting of alkali metal chalcogenides, alkaline earth metal chalcogenides, halides of alkali metals and halides of alkaline earth metals is preferable. It is preferable that the electron injecting layer is constituted with the above substance such as the alkali metal chalcogenide since the electron injecting property can be further improved. Preferable examples of the alkali metal chalcogenide include $Li_2O$, $K_2O$, $Na_2S$, $Na_2Se$ and $Na_2O$. Preferable examples of the alkaline earth metal chalcogenide include CaO, BaO, SrO, BeO, BaS and CaSe. Preferable examples of the halide of an alkali metal include LiF, NaF, KF, LiCl, KCl and NaCl. Preferable examples of the halide of an alkaline earth metal include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides of at least one element selected from Ba, Ca, Sr, Yb, Al, Ga, In, Li, Na, Cd, Mg, Si, Ta, Sb and Zn used singly or in combination of two or more. It is preferable that the inorganic compound constituting the electron transporting layer forms a crystallite or amorphous insulating thin film. When the electron transporting layer is constituted with the insulating thin film described above, a more uniform thin film can be formed, and defects of pixels such as dark spots can be decreased. Examples of the inorganic compound include alkali metal chalcogenides, alkaline earth metal chalcogenides, halides of alkali metals and halides of alkaline earth metals which are described above.

(7) Cathode

For the cathode, a material such as a metal, an alloy, a conductive compound or a mixture of these materials which has a small work function (4 eV or smaller) is used as the electrode material so that electrons can be injected into the electron injecting and transporting layer or the light emitting layer. Examples of the electrode material include sodium, sodium-potassium alloys, magnesium, lithium, magnesium-silver alloys, aluminum/aluminum oxide, aluminum-lithium alloys, indium and rare earth metals.

The cathode can be prepared by forming a thin film of the electrode material described above in accordance with a process such as the vapor deposition process and the sputtering process.

When the light emitted from the light emitting layer is obtained through the cathode, it is preferable that the cathode has a transmittance of the emitted light greater than 10%.

It is also preferable that the sheet resistivity of the cathode is several hundred $\Omega/\square$ or smaller. The thickness of the cathode is, in general, selected in the range of 10 nm to 1 µm and preferably in the range of 50 to 200 nm.

(8) Insulating Layer

Defects in pixels tend to be formed in organic EL device due to leak and short circuit since an electric field is applied to ultra-thin films. To prevent the formation of the defects, it is preferable that a layer of a thin film having the insulating property is inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be used.

(9) Process for Preparing an Organic EL Device

The organic EL device can be prepared by forming the anode, the light emitting layer, the hole injecting and transporting layer where necessary, the electron injecting and transporting layer where necessary and, then, the cathode in the last step in accordance with the above process using the above materials. The organic EL device may be prepared by forming the above layers in the order reverse to that described above, i.e., the cathode being formed in the first step and the anode in the last step.

An embodiment of the process for preparing an organic EL device having a construction in which an anode, a hole injecting layer, a light emitting layer, an electron injecting layer and a cathode are disposed successively on a substrate transmitting light will be described in the following.

On a suitable substrate which transmits light, an anode is prepared by forming a thin film made of a material for the anode in accordance with the vapor deposition process or the sputtering process so that the thickness of the formed thin film is 1 µm or smaller and preferably in the range of 10 to 200 nm. Then, a hole injecting layer is formed on the anode. The hole injecting layer can be formed in accordance with the vacuum vapor deposition process, the spin coating process, the casting process or the LB process as described above. The vacuum vapor deposition process is preferable since a uniform film can be easily obtained and formation of pin holes is suppressed. When the hole injecting layer is formed in accordance with the vacuum vapor deposition process, in general, it is preferable that the conditions are suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 µm, although the conditions of the vacuum vapor deposition are different depending on the used compound (the material for the hole injecting layer) and the crystal structure and the recombination structure of the hole injecting layer to be formed.

For the formation of the light emitting layer on the hole injecting layer formed above, using a desired organic light emitting material, a thin film of the organic light emitting material can be formed in accordance with the vacuum vapor deposition process, the sputtering process, the spin coating process or the casting process. The vacuum vapor deposition process is preferable since a uniform film can be easily obtained and formation of pin holes is suppressed. When the light emitting layer is formed in accordance with the vacuum vapor deposition process, in general, the conditions of the vacuum vapor deposition process can be selected in the same ranges as those described for the vacuum vapor deposition of the hole injecting layer although the conditions are different depending on the used compound.

The electron injecting layer is formed on the light emitting layer formed above. Similarly to the hole injecting layer and the light emitting layer, it is preferable that the electron injecting layer is formed in accordance with the vacuum vapor deposition process since a uniform film must be obtained. The conditions of the vacuum vapor deposition can be selected in the same ranges as those described for the vacuum vapor deposition of the hole injecting layer and the light emitting layer.

Although specific conditions are different depending on whether the nitrogen-containing heterocyclic derivative of the present invention is used for the light emitting zone or the electron transporting zone, the nitrogen-containing heterocyclic derivative of the present invention can be vapor deposited simultaneously in combination with other materials when the vacuum vapor deposition process is used. When the spin coating process is used, the derivative of the present invention can be used in combination with other materials by mixing the materials together.

The cathode is formed on the electron injecting layer formed above in the last step, and the organic EL device can be obtained.

The cathode is constituted with a metal and can be formed in accordance with the vacuum vapor deposition process or the sputtering process. It is preferable that the vacuum vapor deposition process is used in order to prevent formation of damages on the lower organic layers during the formation of the film.

In the above preparation of the organic EL device, it is preferable that the above layers from the anode to the cathode are formed successively while the preparation system is kept in a vacuum after being evacuated once.

The process for forming the layers in the organic EL device of the present invention is not particularly limited. A conventional process such as the vacuum vapor deposition process and the spin coating process can be used. The organic thin film layer comprising the compound represented by general formula (1) shown above used for the organic EL device can be formed in accordance with a conventional process such as the vacuum vapor deposition process and the molecular beam epitaxy process (the MBE process) or, using a solution prepared by dissolving the compounds into a solvent, in accordance with a coating process such as the dipping process, the spin coating process, the casting process, the bar coating process and the roll coating process.

The thickness of each layer in the organic thin film layer in the organic EL device of the present invention is not particularly limited. In general, defects such as pin holes tend to be formed when the thickness is excessively small and, when the thickness is excessively great, application of an excessively high voltage is necessary and the efficiency decreases. Therefore, in general, a thickness in the range of several nanometers to 1 μm is preferable.

When a direct voltage is applied to the organic EL device, emission of light can be observed under application of a voltage of 5 to 40 V in the condition such that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES

Synthesis Example 1

(1-1) Synthesis of Intermediate 1

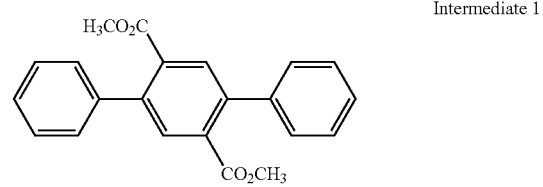

Into a 1 liter three-necked flask, 35 g (0.1 mole) of dimethyl 2,5-dibromoterephthalate, 27 g (0.22 moles) of phenyl boronic acid, 5.7 g (5 mmole) of tetrakis(triphenylphosphine)palladium(0), 200 ml of toluene and a solution prepared by dissolving 32 g (0.3 moles) of sodium carbonate into 150 ml of water were placed under the stream of argon, and the resultant mixture was heated under the refluxing condition for 8 hours. After the reaction was completed, the organic layer was washed with water and dried with magnesium sulfate, and the solvent was removed by distillation using a rotary evaporator. The obtained crude crystals were recrystallized from ethanol, and 27 g of Intermediate 1 of the object compound was obtained (white crystals; the yield: 80%).

(1-2) Synthesis of Intermediate 2

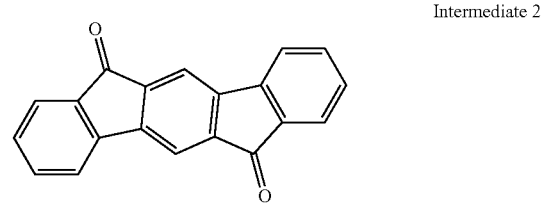

Into a 1 liter flask, 17 g (0.05 moles) of Intermediate 1 and 200 ml of 80% sulfuric acid were placed, and the obtained solution was heated at 180° C. for 3 hours under stirring. After the reaction was completed, sulfuric acid was removed by liquid separation. After methylene chloride was added, the resultant solution was washed with an aqueous solution of sodium hydrogencarbonate and dried with magnesium sulfate. The solvent was removed by distillation using a rotary evaporator, and a crude reaction product was obtained. The crude reaction product was purified in accordance with the column chromatography (silica gel; hexane:ethyl acetate=95:5), and 10 g of Intermediate 2 of the object compound was obtained (gray crystals; the yield: 70%).

(1-3) Synthesis of Intermediate 3

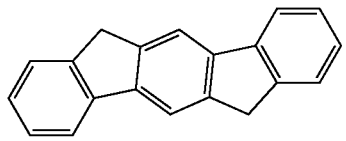

Intermediate 3

Into a 1 liter flask, 10 g (0.035 moles) of Intermediate 2, 8.8 ml (0.175 moles) of hydrazine monohydrate, 12 g (0.18 moles) of potassium hydroxide and 300 ml of diethylene glycol were placed, and the obtained mixture was heated at 200° C. for 2 hours under stirring. After the reaction was completed, water was added, and the formed precipitates were separated by filtration. The crude reaction product was reprecipitated from hexane:chloroform, and 4.5 g of Intermediate 3 of the object compound was obtained (a light brown solid substance; the yield: 50%).

(1-4) Synthesis of Intermediate 4

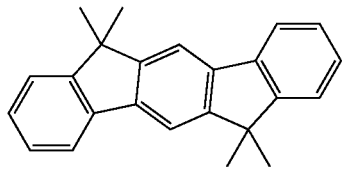

Intermediate 4

Into a 300 ml three-necked flask, 4 g (0.015 moles) of Intermediate 3, 9 g (0.08 moles) of t-butoxypotassium and 100 ml of DMSO were placed under the stream of argon, and the reaction system was cooled at 5° C. After 11 g (0.08 moles) of methyl iodide was slowly added dropwise, the resultant mixture was stirred for one night. After the reaction was completed, water was added, and the organic layer was separated by extraction with ethyl acetate, washed with a saturated aqueous solution of sodium chloride and dried with magnesium sulfate. The solvent was removed by distillation using a rotary evaporator, and a crude reaction product was obtained. The crude reaction product was purified in accordance with the column chromatography (silica gel; hexane:ethyl acetate=95:5), and 4.6 g of Intermediate 4 of the object compound was obtained (white crystals; the yield: 95%).

(1-5) Synthesis of Intermediate 5

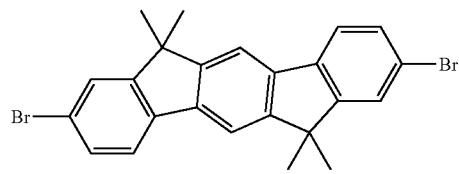

Intermediate 5

Into 200 ml flask, 3.1 g (10 mmole) of Intermediate 4 and 20 ml of chloroform were placed. To the obtained solution, 3.2 g (20 mmole) of bromine was slowly added dropwise, and the resultant mixture was stirred at the room temperature for 2 hours. After the reaction was completed, an aqueous solution of sodium thiosulfate was added to the reaction fluid, and the organic layer was separated, washed with water and a saturated aqueous solution of sodium chloride and dried with sodium sulfate. The solvent was removed by distillation using a rotary evaporator. The obtained crude crystals were recrystallized from ethanol, and 3.7 g of Intermediate 5 of the object compound was obtained (white crystals; the yield: 80%).

(1-6) Synthesis of Intermediate 6

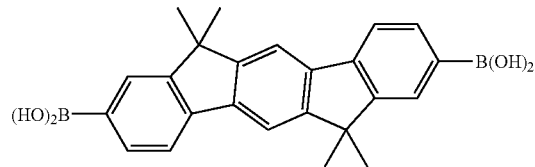

Intermediate 6

Into a 3 liter three-necked flask, 10 g (0.021 moles) of Intermediate 5 and 200 ml of THF were placed under the stream of argon, and the obtained solution was cooled at −65° C. To the cooled solution, 47 ml of a solution of n-butyl-lithium (0.047 moles, a 1 mole/liter hexane solution) was slowly added. After the reaction fluid was stirred at −70° C. for 6 hours, 24 g (0.13 moles) of boronic acid triisopropoxide was slowly added at −65° C. The resultant fluid was stirred at −70° C. for 1 hour and then at the room temperature for one night. After the reaction was completed, dilute hydrochloric acid was added to the reaction fluid to adjust pH at 3, and the organic layer was separated, washed with a saturated aqueous solution of sodium chloride and dried with magnesium sulfate. The solvent was removed by distillation using a rotary evaporator, and ethyl acetate was added to the residue. The obtained crystals were separated by filtration and washed with hexane three times, and 5.9 g of Intermediate 6 of the object compound was obtained (white crystals; the yield: 69%).

(1-7) Synthesis of Compound (1)

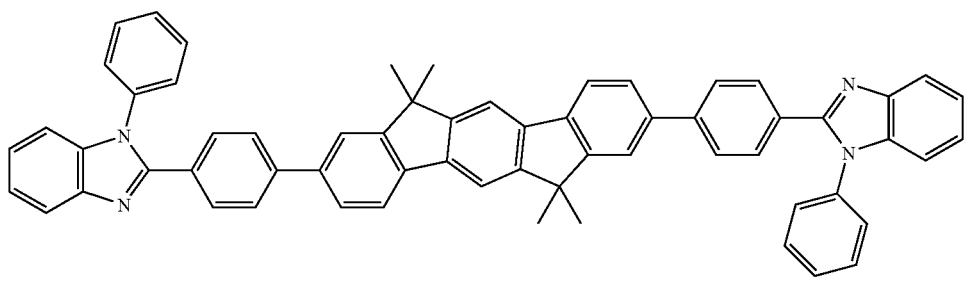

Compound (1)

Into a 300 ml three-necked flask, 2.0 g (5.0 mmole) of Intermediate 6, 3.9 g (11 mmole) of 2-(4-bromophenyl)-1-phenylbenzimidazole, 0.23 g (0.20 mmole) of tetrakis(triphenylphosphine)palladium(0), 50 ml of 1,2-dimethoxyethane and 15 ml (30 mmole) of a 2 M aqueous solution of sodium carbonate were placed under the stream of argon, and the resultant mixture was heated under the refluxing condition for 8 hours. After the reaction was completed, the organic layer was washed with water and dried with magnesium sulfate, and the solvent was removed by distillation using a rotary evaporator. The obtained crude crystals were washed with 50 ml of toluene and 100 ml of methanol, and 3.4 g of a light yellow powder substance was obtained. The obtained substance was identified to be Compound (1) by the measurement of the field desorption mass spectrum (FD-MS) (the yield: 80%).

Synthesis Example 2

Synthesis of Compound (2)

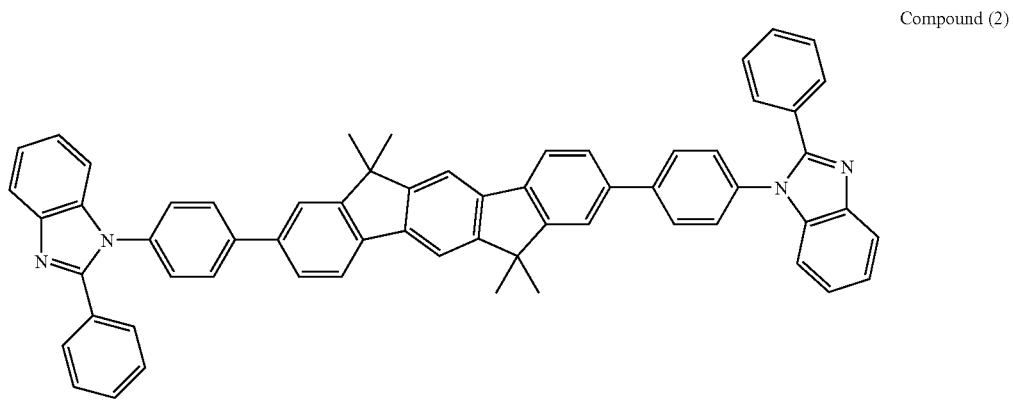

Compound (2)

In accordance with the same procedures as those conducted in the synthesis of Compound (1) except that 2-phenyl-1-(4-bromophenyl)benzimidazole was used in place of 2-(4-bromophenyl)-1-phenylbenzimidazole, Compound (2) was obtained as a light yellow powder substance. The amount was 3.0 g (the yield: 70%). The obtained substance was identified to be Compound (2) by the measurement of the field desorption mass spectrum (FD-MS).

Synthesis Example 3

Synthesis of Compound (3)

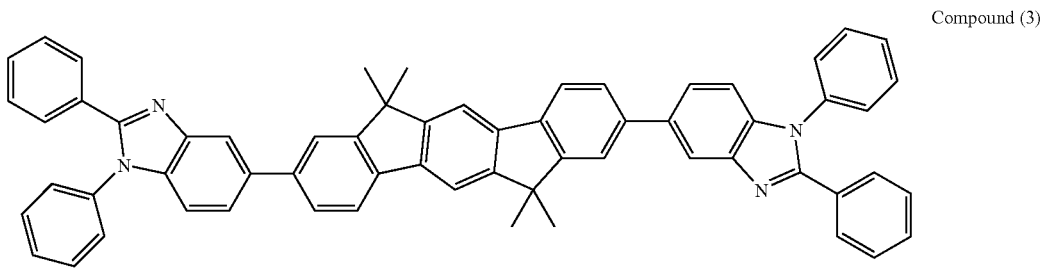

Compound (3)

In accordance with the same procedures as those conducted in the synthesis of Compound (1) except that 5-bromo-1,2-diphenylbenzimidazole was used in place of 2-(4-bromophenyl)-1-phenylbenzimidazole, Compound (3) was obtained as a light yellow powder substance. The amount was 3.5 g (the yield: 82%). The obtained substance was identified to be Compound (3) by the measurement of the field desorption mass spectrum (FD-MS).

Synthesis Example 4

(4-1) Synthesis of Intermediate 7

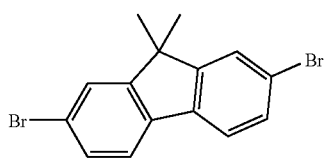

Intermediate 7

Into a 3 liter three-necked flask, 32 g (0.1 mole) of 2,7-dibromofluorene, 27 g (0.24 moles) of t-butoxypotassium and 500 ml of DMSO were placed under the stream of argon, and the reaction system was cooled at 5° C. After 34 g (0.24 moles) of methyl iodide was slowly added dropwise, the resultant mixture was stirred for one night. After the reaction was completed, water was added, and the organic layer was separated by extraction with ethyl acetate, washed with a saturated aqueous solution of sodium chloride and dried with magnesium sulfate. The solvent was removed by distillation using a rotary evaporator, and a crude reaction product was obtained. The crude reaction product was purified in accordance with the column chromatography (silica gel; hexane:ethyl acetate=95:5), and 34 g of Intermediate 7 of the object compound was obtained (white crystals; the yield: 98%).

(4-2) Synthesis of Intermediate 8

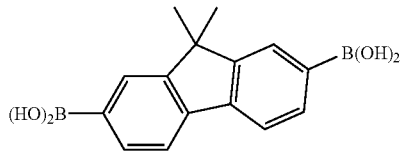

Intermediate 8

Into a 3 liter three-necked flask, 35 g (0.1 mole) of Intermediate 7 and 1 liter of THF were placed under the stream of argon, and the obtained solution was cooled at −65° C. To the cooled solution, 220 ml of a solution of n-butyllithium (0.22 moles, a 1 mole/liter hexane solution) was slowly added. After the reaction fluid was stirred at −70° C. for 6 hours, 45 g (0.24 moles) of boronic acid triisopropoxide was slowly added at −65° C. The resultant fluid was stirred at −70° C. for 1 hour and then at the room temperature for one night. After the reaction was completed, dilute hydrochloric acid was added to the reaction fluid to adjust pH at 3, and the organic layer was separated, washed with a saturated aqueous solution of sodium chloride and dried with magnesium sulfate.

The solvent was removed by distillation using a rotary evaporator, and ethyl acetate was added to the residue. The obtained crystals were separated by filtration and washed with hexane three times, and 20 g of Intermediate 8 of the object compound was obtained (white crystals; the yield: 70%).

(4-3) Synthesis of Intermediate 9

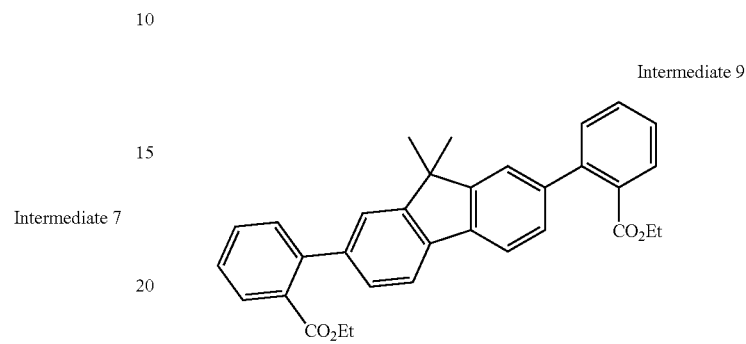

Intermediate 9

Into a 1 liter three-necked flask, 14 g (0.05 moles) of Intermediate 8, 25 g (0.11 moles) of ethyl 2-bromobenzoate, 2.8 g (5 mmole) of tetrakistriphenylphosphinepalladium(0), 200 ml of toluene and a solution prepared by dissolving 16 g (0.15 moles) of sodium carbonate into 150 ml of water were placed under the stream of argon, and the resultant mixture was heated under the refluxing condition for 8 hours. After the reaction was completed, the organic layer was washed with water and dried with magnesium sulfate, and the solvent was removed by distillation using a rotary evaporator. The obtained crude crystals were recrystallized from ethanol, and 12 g of Intermediate 9 of the object compound was obtained (white crystals; the yield: 50%).

(4-4) Synthesis of Intermediate 10

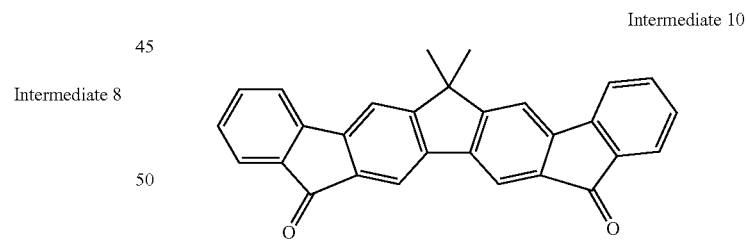

Intermediate 10

Into a 1 liter flask, 12 g (0.025 moles) of Intermediate 9 and 200 ml of 80% sulfuric acid were placed, and the obtained solution was heated at 180° C. for 3 hours under stirring. After the reaction was completed, sulfuric acid was removed by liquid separation. After methylene chloride was added, the resultant solution was washed with an aqueous solution of sodium hydrogencarbonate and dried with magnesium sulfate. The solvent was removed by distillation using a rotary evaporator, and a crude reaction product was obtained. The crude reaction product was purified in accordance with the column chromatography (silica gel; hexane:ethyl acetate=95:

5), and 6.2 g of Intermediate 10 of the object compound was obtained (gray crystals; the yield: 60%).

(4-5) Synthesis of Intermediate 11

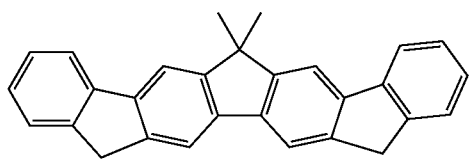

Intermediate 11

Into a 500 ml flask, 6 g (0.016 moles) of Intermediate 10, 4 ml (0.075 moles) of hydrazine monohydrate, 5 g (0.076 moles) of potassium hydroxide and 100 ml of diethylene glycol were placed, and the obtained mixture was heated at 200° C. for 2 hours under stirring. After the reaction was completed, water was added, and the formed precipitates were separated by filtration. The crude reaction product was reprecipitated from hexane:chloroform, and 2.9 g of Intermediate 11 of the object compound was obtained (a light brown solid substance; the yield: 50%).

(4-5) Synthesis of Intermediate 12

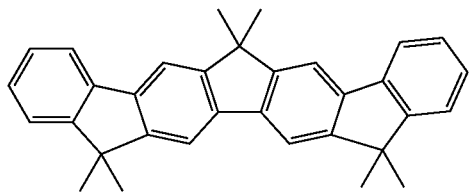

Intermediate 12

Into a 300 ml three-necked flask, 2.9 g (7.5 mmole) of Intermediate 11, 3.8 g (40 mmole) of t-butoxypotassium and 100 ml of DMSO were placed under the stream of argon, and the reaction system was cooled at 5° C. After 5.6 g (40 moles) of methyl iodide was slowly added dropwise, the resultant mixture was stirred for one night. After the reaction was completed, water was added, and the organic layer was separated by extraction with ethyl acetate, washed with a saturated aqueous solution of sodium chloride and dried with magnesium sulfate. The solvent was removed by distillation using a rotary evaporator, and a crude reaction product was obtained. The crude reaction product was purified in accordance with the column chromatography (silica gel; hexane:ethyl acetate=95:5), and 3.0 g of Intermediate 12 of the object compound was obtained (white crystals; the yield: 90%).

(4-5) Synthesis of Intermediate 13

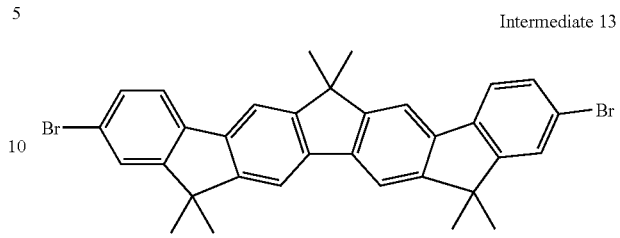

Intermediate 13

Into 200 ml flask, 2.2 g (5 mmole) of Intermediate 12 and 20 ml of chloroform were placed. To the obtained solution, 1.6 g (10 mmole) of bromine was slowly added dropwise, and the resultant mixture was stirred at the room temperature for 2 hours. After the reaction was completed, an aqueous solution of sodium thiosulfate was added to the reaction fluid. The organic layer was separated, washed with water and a saturated aqueous solution of sodium chloride and dried with sodium sulfate. The solvent was removed by distillation using a rotary evaporator. The obtained crude crystals were recrystallized from ethanol, and 2.1 g of Intermediate 13 of the object compound was obtained (white crystals; the yield: 70%).

(4-6) Synthesis of Intermediate 14

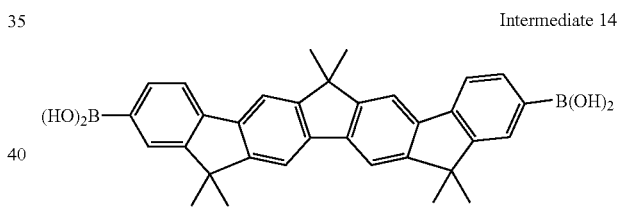

Intermediate 14

Into a 3 liter three-necked flask, 2.1 g (3.6 mmoles) of Intermediate 13 and 50 ml of THF were placed under the stream of argon, and the obtained solution was cooled at −65° C. To the cooled solution, 8.0 ml of a solution of n-butyllithium (8.0 mmoles, a 1 mole/liter hexane solution) was slowly added. After the reaction fluid was stirred at −70° C. for 6 hours, 4.0 g (21 mmole) of boronic acid triisopropoxide was slowly added at −65° C. The resultant fluid was stirred at −70° C. for 1 hour and then at the room temperature for one night. After the reaction was completed, dilute hydrochloric acid was added to the reaction fluid to adjust pH at 3, and the organic layer was separated, washed with a saturated aqueous solution of sodium chloride and dried with magnesium sulfate. The solvent was removed by distillation using a rotary evaporator, and ethyl acetate was added to the residue. The obtained crystals were separated by filtration and washed with hexane three times, and 1.1 g of Intermediate 14 of the object compound was obtained (white crystals; the yield: 59%).

(4-7) Synthesis of Compound (4)

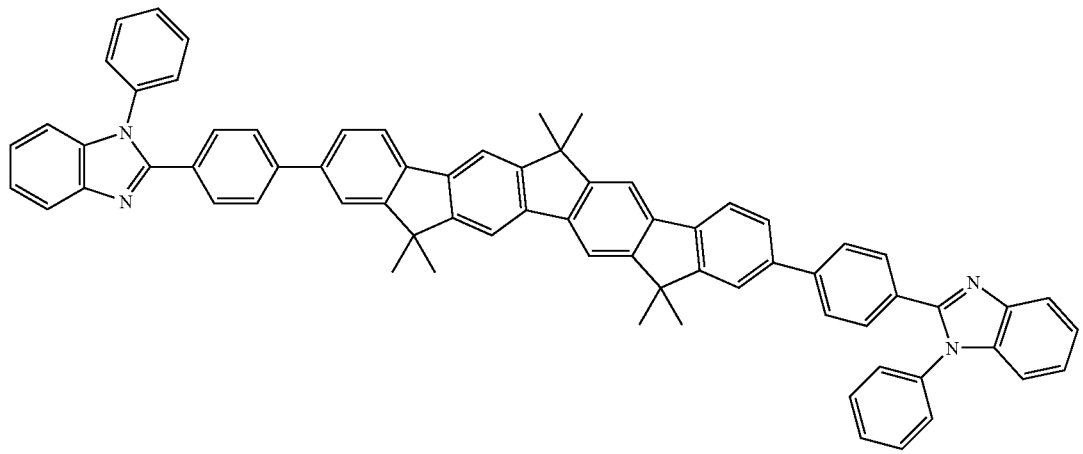

Compound (4)

Into a 300 ml three-necked flask, 1.1 g (2.1 mmole) of Intermediate 14, 1.6 g (4.6 mmole) of 2-(4-bromophenyl)-1-phenylbenzimidazole, 0.10 g (0.09 mmole) of tetrakis(triphenylphosphine)palladium(0), 20 ml of 1,2-dimethoxyethane and 6.5 ml (13 mmole) of a 2 M aqueous solution of sodium carbonate were placed under the stream of argon, and the resultant mixture was heated under the refluxing condition for 8 hours. When the reaction was completed, the organic layer was washed with water and dried with magnesium sulfate, and the solvent was removed by distillation using a rotary evaporator. The obtained crude crystals were washed with 50 ml of toluene and 100 ml of methanol, and 1.6 g of a light yellow powder substance was obtained. The obtained substance was identified to be Compound (4) by the measurement of the field desorption mass spectrum (FD-MS) (the yield: 78%).

Example 1

Preparation of an Organic EL Device (1) Preparation of an Organic EL Device

On a glass substrate of a 25 mm×75 mm×1.1 mm size, a transparent electrode made of indium tin oxide and having a thickness of 130 nm was formed. The obtained glass substrate was cleaned by application of ultrasonic wave in isopropyl alcohol and by exposure to ultraviolet light and ozone.

The cleaned glass substrate having the transparent electrode was attached to a substrate holder in a vapor deposition tank of a vacuum vapor deposition apparatus. After the pressure in the vacuum tank was reduced to $1 \times 10^{-3}$ Pa, a hole injecting layer, a hole transporting layer, a light emitting layer, an electron transporting layer, an electron injecting layer and a cathode layer were successively laminated to the anode layer under the following conditions, and an organic EL device was prepared.

Hole injecting layer: N',N'''-bis[4-(diphenylamino)phenyl]-N',N'-diphenylbiphenyl-4,4'-diamine; the condition of the vapor deposition: 2 nm/sec; the thickness of the film: 60 nm Hole transporting layer: N,N'-di(naphthalen-1-yl)-N,N'-diphenyl-benzidine; the condition of the vapor deposition: 2 nm/sec; the thickness of the film: 20 nm Light emitting layer: simultaneous vapor deposition of the following host and dopant; the thickness of the film: 40 nm (host:dopant=40:2)

host: 2-t-butyl-9,10-diphenylanthracene; the condition of the vapor deposition: 2 nm/sec dopant: tetrakis(2-naphthyl)-4,4'-diaminostilbene; the condition of the vapor deposition: 0.2 nm/sec Electron transporting layer: Compound (1); the condition of the vapor deposition: 2 nm/sec; the thickness of the film: 20 nm Electron injecting layer: lithium fluoride; the condition of the vapor deposition: 0.1 nm/sec; the thickness of the film: 1 nm Cathode layer: aluminum; the condition of the vapor deposition: 2 nm/sec; the thickness of the film: 200 nm (2) Evaluation of an Organic EL Device The prepared organic EL device was examined by passing electric current. It was confirmed that the luminance of emitted light was 500 cd/m$^2$ under application of a voltage of 6.0 V, and the color of the emitted light was blue. When the device was driven under a constant current at the initial luminance of emitted light of 500 cd/m$^2$, the time for 10% decrease in the luminance was 100 hours. The obtained results are shown in Table 1. When the above device was kept at 85° C. for 500 hours, no change in the driving voltage was found.

Examples 2 to 4

Organic EL devices were prepared in accordance with the same procedures as those conducted in Example 1 except that Compound (2) to Compound (4) were used for the electron transporting layer in Examples 2 to 4, respectively, in place of Compound (1) used in Example 1. As shown by the results in Table 1, emission of blue light was observed in all cases. The luminance of emitted light was 480 to 510 cd/m$^2$, and the time for 10% decrease in the luminance was 90 to 110 hours.

TABLE 1

| | Example 1 | Example 2 | Example 3 | Example 4 |
|---|---|---|---|---|
| Electron transporting material | (1) | (2) | (3) | (4) |
| Driving voltage (V) | 6.5 | 6.5 | 6.5 | 6.5 |
| Color of emitted light | blue | blue | blue | blue |
| Luminance of emitted light (cd/m$^2$) | 500 | 510 | 490 | 480 |
| Time for 10% decrease in luminance (hour) | 100 | 110 | 90 | 100 |
| After being kept at 85° C. for 500 hours | no change in driving voltage | no change in driving voltage | no change in driving voltage | no change in driving voltage |

Comparative Example 1 and 2

Organic EL devices were prepared in accordance with the same procedures as those conducted in Example 1 except that the following compounds were used for the electron transporting layer in Comparative Examples 1 and 2 in place of Compound (1) used in Example 1.

As shown by the results in Table 2, emission of blue light was observed in all cases. The luminance of emitted light was 400 to 430 cd/m$^2$, and the time for 10% decrease in the luminance was 50 to 60 hours. The driving voltage increased by 1 V or greater after the devices were kept at 85° C. for 500 hours.

Comparative Example 1

Compound (A) tris(8-hydroxyquinolino)-aluminum; the thickness of the film: 20 nm

Comparative Example 2

Compound (B) tris(2-(1-phenylbenz-imidazolyl))benzene; the thickness of the film: 20 nm

TABLE 2

Compound (A)

Compound (B)

| | Comparative Example 1 | Comparative Example 2 |
|---|---|---|
| Electron transporting material | (A) | (B) |
| Driving voltage (V) | 6.5 | 6.5 |
| Color of emitted light | blue | blue |
| Luminance of emitted light (cd/m$^2$) | 400 | 430 |
| Time for 10% decrease in luminance (hour) | 50 | 60 |
| After being kept at 85° C. for 500 hours | increase in driving voltage of 1 V or greater | increase in driving voltage of 1 V or greater |

It is shown by the above results that the half life is increased remarkably under application of a low voltage by using the material of the present invention as the electron transporting material.

INDUSTRIAL APPLICABILITY

As described specifically in the above, it has been found that the driving voltage can be decreased and the life can be increased remarkably by using the nitrogen-containing heterocyclic derivative of the present invention as the electron transporting material. Therefore, the organic EL device of the present invention is advantageously used in practical applications and highly valuable as the light source such as the planar light emitting body of wall televisions and the back light for displays. The derivative can be used for organic EL devices and electron transporting materials, and also for charge transporting materials in electronic photosensitive materials and organic semiconductors.

What is claimed is:

1. A compound represented by a formula selected from the group consisting of (1-a), (1-b), (1-c), (2-a), (2-b), and (2-c)

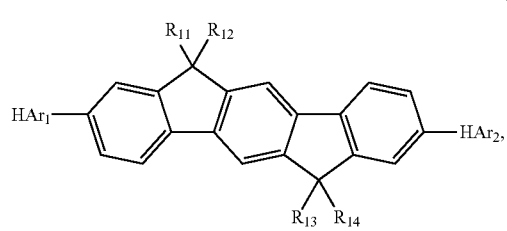

(1-a)

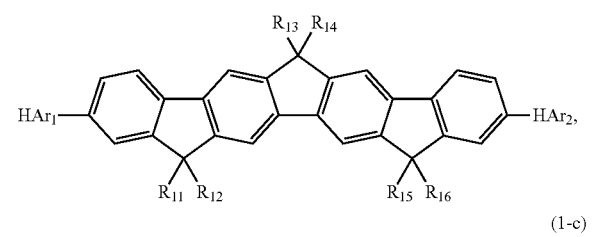

(1-b)

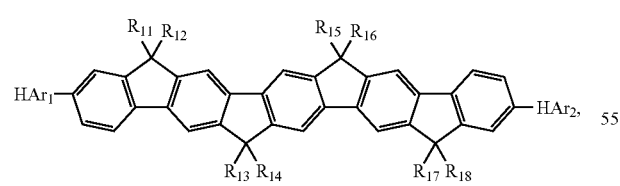

(1-c)

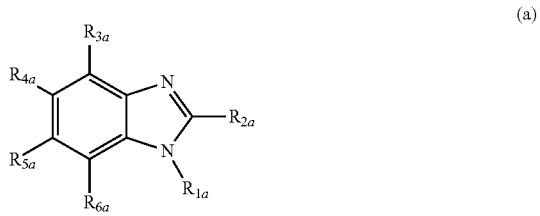

(2-a)

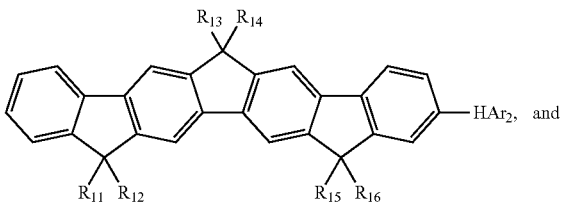

(2-b)

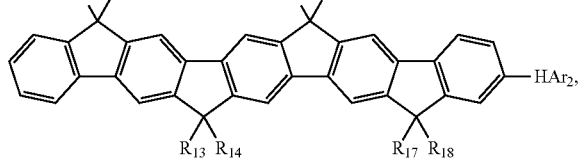

(2-c)

wherein $R_{11}$ to $R_{18}$ each independently represent a hydrogen atom, a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted with a substituted or unsubstituted aryl group having 5 to 50 ring atoms, a halogen atom, a cyano group, a nitro group, a hydroxy group or a carboxy group;

$HAr_1$ and $HAr_2$ each independently represent a monovalent group formed by removing a hydrogen atom from any one of $R_{1a}$ to $R_{6a}$ in formula (a):

(a)

in formula (a), $R_{1a}$ to $R_{6a}$ each independently representing a hydrogen atom, a substituted or unsubstituted aryl group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 ring atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, an amino group substituted with a substituted or unsubstituted aryl group having 5 to 50 ring atoms, a halogen atom, a cyano group, a nitro group, a hydroxy group or a carboxy group.

2. The compound according to claim 1, represented by formula (1-a).

3. The compound according to claim 1, represented by formula (1-b).

4. The compound according to claim 1, represented by formula (1-c).

5. The compound according to claim 1, represented by formula (2-a).

6. The compound according to claim 1, represented by formula (2-b).

7. The compound according to claim 1, represented by formula (2-c).

* * * * *